United States Patent
Ban et al.

(10) Patent No.: US 12,193,897 B2
(45) Date of Patent: Jan. 14, 2025

(54) ZIRCONIA MILL BLANK FOR DENTAL CUTTING AND MACHINING AND PREPARING METHOD THEREOF, AND TRANSPARENCY IMPROVING LIQUID FOR ZIRCONIA MILL BLANK FOR DENTAL CUTTING AND MACHINING AND USING METHOD THEREOF

(71) Applicant: SHOFU INC., Kyoto (JP)

(72) Inventors: Seiji Ban, Aichi (JP); Shuhei Takahashi, Kyoto (JP); Toshio Kitamura, Kyoto (JP); Rieko Aiba, Kyoto (JP)

(73) Assignee: SHOFU INC., Kyoto (JP)

( * ) Notice: Subject to any disclaimer, the term of this patent is extended or adjusted under 35 U.S.C. 154(b) by 1450 days.

(21) Appl. No.: 16/487,129

(22) PCT Filed: Feb. 20, 2018

(86) PCT No.: PCT/JP2018/006090
§ 371 (c)(1),
(2) Date: Jan. 8, 2020

(87) PCT Pub. No.: WO2018/155459
PCT Pub. Date: Aug. 30, 2018

(65) Prior Publication Data
US 2020/0113658 A1    Apr. 16, 2020

(30) Foreign Application Priority Data

Feb. 21, 2017 (JP) ................................ 2017-029797
Mar. 31, 2017 (JP) ................................ 2017-071954
Dec. 19, 2017 (JP) ................................ 2017-242860

(51) Int. Cl.
A61C 13/00    (2006.01)
A61C 5/73    (2017.01)
C04B 35/48    (2006.01)
C04B 41/87    (2006.01)

(52) U.S. Cl.
CPC ............ *A61C 13/0022* (2013.01); *A61C 5/73* (2017.02); *C04B 35/48* (2013.01); *C04B 41/87* (2013.01); *C04B 2235/3246* (2013.01); *C04B 2235/94* (2013.01); *Y10T 428/12229* (2015.01)

(58) Field of Classification Search
None
See application file for complete search history.

(56) References Cited

U.S. PATENT DOCUMENTS

| | | | |
|---|---|---|---|
| 4,199,563 | A | 4/1980 | Muhlemann |
| 5,968,424 | A | 10/1999 | Shimosawa et al. |
| 6,709,694 | B1 * | 3/2004 | Suttor ............... A61K 6/818 427/372.2 |
| 9,962,247 | B2 * | 5/2018 | Fujisaki ............ C01F 17/218 |
| 2008/0206551 | A1 | 8/2008 | Hartman et al. |
| 2011/0236860 | A1 | 9/2011 | Jahns et al. |
| 2012/0252654 | A1 | 10/2012 | Kariya et al. |
| 2013/0115365 | A1 | 5/2013 | Wang et al. |
| 2015/0157430 | A1 | 6/2015 | Hauptmann et al. |
| 2015/0223917 | A1 | 8/2015 | Herrmann et al. |
| 2016/0354186 | A1 | 12/2016 | Kim et al. |
| 2017/0143458 | A1 | 5/2017 | Fujisaki et al. |
| 2017/0245970 | A1 | 8/2017 | Jung et al. |

FOREIGN PATENT DOCUMENTS

| | | |
|---|---|---|
| CN | 102344285 | 2/2012 |
| CN | 102579148 | 7/2012 |
| CN | 102584225 | 7/2012 |
| CN | 105130431 | 12/2015 |
| DE | 10 2008 026 980 | 12/2009 |
| DE | 10 2015 103 439 | 9/2016 |
| DE | 102015103439 A1 * | 9/2016 |
| EP | 2 573 060 | 3/2013 |
| JP | 53-139394 | 12/1978 |

(Continued)

OTHER PUBLICATIONS https://www.americanelements.com/erbium-chloride-10025-75-9 (Year: 2015).*
Machine translation of DE 102015103439 A1 via the EPO translated Dec. 1, 2023 (Year: 2015).*
International Search Report issued Apr. 10, 2018 in International Application No. PCT/JP2018/006090, with English-language translation.
Chemistry Dictionary 4, reduced edition, Oct. 15, 1963, p. 773. Cited in International Search Report (item CA).
Written Opinion of the International Searching Authority issued Apr. 10, 2018 in International Application No. PCT/JP2018/006090, with English-language translation.

(Continued)

*Primary Examiner* — Elizabeth Collister
(74) *Attorney, Agent, or Firm* — Wenderoth, Lind & Ponack, L.L.P.

(57) ABSTRACT

To provide a zirconia perfect sintered body which has a chroma of an excellent color tone and excellent translucency as compared with a zirconia mill blank for dental cutting and machining prepared from a zirconia raw material powder containing various stabilizing materials while maintaining high strength, and does not cause deformation. The zirconia mill blank of the present invention is a semi-fired zirconia mill blank for dental cutting and machining containing a semi-fired body of a ceramic particle, the zirconia mill blank for dental cutting and machining contains zirconium oxide, a stabilizing material consisting of an oxide, and a water-soluble compound salt which contains at least one element selected from calcium, magnesium and a rare earth element and is not an oxide, the content of the stabilizing material in terms of the oxide in the semi-fired body of the ceramic particle is within a range of 2 to 7 mol %, and the content of the water-soluble compound salt in the zirconia mill blank for dental cutting and machining is within a range of 0.1 to 3.5 mol %.

23 Claims, No Drawings

(56) References Cited

FOREIGN PATENT DOCUMENTS

| | | |
|---|---|---|
| JP | 60-235762 | 11/1985 |
| JP | 11-267139 | 10/1999 |
| JP | 2002-536280 | 10/2002 |
| JP | 2012-211063 | 11/2012 |
| JP | 2013-529599 | 7/2013 |
| JP | 5608976 | 9/2014 |
| JP | 2015-532629 | 11/2015 |
| JP | 2015-536904 | 12/2015 |
| WO | 2014/073343 | 5/2014 |
| WO | 2015/199018 | 12/2015 |

OTHER PUBLICATIONS

Extended European Search Report issued Feb. 12, 2021 in European Patent Application No. 18756914.0.
Office Action issued Aug. 27, 2021 in Chinese Patent Application No. 201880013137.7, with English-language translation.
Office Action issued Mar. 24, 2022 in Japanese Patent Application No. 2019-501354, with English-language translation.

\* cited by examiner

ZIRCONIA MILL BLANK FOR DENTAL CUTTING AND MACHINING AND PREPARING METHOD THEREOF, AND TRANSPARENCY IMPROVING LIQUID FOR ZIRCONIA MILL BLANK FOR DENTAL CUTTING AND MACHINING AND USING METHOD THEREOF

CROSS-REFERENCE TO RELATED APPLICATIONS

This application is based on and claims the benefit of priorities from Japanese Patent Application Serial No. 2017-29797 (filed on Feb. 21, 2017), Japanese Patent Application Serial No. 2017-71954 (filed on Mar. 31, 2017) and Japanese Patent Application Serial No. 2017-242860 (filed on Dec. 19, 2017), the contents of which are hereby incorporated by reference in their entirety.

TECHNICAL FIELD

The present invention relates to a zirconia mill blank for dental cutting and machining and a preparing method thereof, and a transparency improving liquid for zirconia mill blank for dental cutting and machining and a using method thereof.

BACKGROUND ART

In the conventional dental treatment of a defect part of the dental crown, the prosthetic restoration using a casting crown bridge and an artificial tooth has been performed generally. Specific examples include a clinical applications of a porcelain baked crown bridge which reproduces a tooth crown shape by baking porcelain on a surface of a metal frame made from a casting alloy for porcelain baking.

In addition, from the point of view of the metal allergy and the price remarkable rise to depend on the noble metal market price and from the point of view of aesthetic property which can imitate the color tone of the natural tooth, a prosthesis device, which is so-called all ceramics, prepared by the dipping method using such as alumina, aluminosilicate glass, lithium disilicate glass or by the press method using ceramic ingot, has attracted attention.

In recent years, techniques to prepare a prosthesis device by the cutting and machining which uses the dental CAD/CAM system spread rapidly and it has been becoming possible to easily prepare prosthetic devices by cutting and machining the blanks such as a block and a disk which are made of zirconia, alumina, aluminosilicate glass, and lithium disilicate glass.

In particular, zirconia has been clinically applied in various cases because of its high strength. The perfect sintered zirconia (hereinafter, also referred to as "zirconia perfect sintered body" in the present specification) has high hardness and therefore cannot be cut and machined using a dental CAD/CAM system. Thus, a so-called pre-sintered body has been used as a zirconia mill blank for dental cutting and machining, which is not fully sintered but is calcined at a low firing temperature to adjust to a hardness that enables to cut.

A general zirconia mill blank for dental cutting and machining is prepared by molding a zirconia raw material powder by press molding or the like and then calcining at about 800 to 1200° C.

The properties of the zirconia mill blank for dental cutting and machining, that is, the properties of the zirconia perfect sintered body (fully sintered body) are influenced by the properties of the used zirconia raw material powder.

For example, Patent Document 1 discloses a zirconia blank (mill blank) for dental cutting and machining prepared by using a zirconia raw material powder containing 3 mol % of yttrium, and a zirconia perfect sintered body prepared from the zirconia blank. Since this sintered body has high strength, it is clinically applied in the frame of 4 or more unit bridges. However, since this sintered body has low translucency, it is difficult to reproduce the color tone similar to that of natural tooth.

Patent Document 2 discloses a zirconia mill blank for dental cutting and machining prepared by using a zirconia raw material powder containing 3 mol % of yttrium with a reduced alumina content and a zirconia perfect sintered body prepared from the zirconia mill blank for dental cutting and machining. Since the translucency is improved in the perfect sintered body while maintaining high strength, the perfect sintered body is clinically applied in a long span bridge of 4 or more unit, molar part full crown and the like. However, since translucency is insufficient in the perfect sintered body, it has been difficult to apply to the case where high aesthetics is required such as a front tooth portion.

Patent Document 3 discloses a zirconia blank for dental cutting and machining prepared by using a zirconia raw material powder containing 4 to 6.5 mol % of yttrium and a zirconia perfect sintered body prepared from the zirconia blank. Since the perfect sintered body has high translucency, the perfect sintered body is clinically applied to the case where high aesthetics is required such as a front tooth portion. However, although translucency is high, since the strength is insufficient, there has been a problems such as difficulty in application to a long span bridge of 4 units or more and breakage of an incisal portion.

As described above, in the zirconia perfect sintered body prepared by using the zirconia raw material powder containing 4 to 6.5 mol % of yttrium, although the transparency is increased, the strength is decreased. On the other hand, in the zirconia perfect sintered body prepared by using the zirconia raw material powder containing 3 mol % of yttrium, although the strength is increased, the transparency is decreased. Therefore, the characteristics of the zirconia perfect sintered body depend on the yttrium content of the zirconia raw material powder, and the translucency and the strength are in a trade-off relationship.

In order to solve these problems, a zirconia blank for dental cutting and machining in which zirconia raw material powders having different yttrium contents are laminated has been clinically applied for achieving both the translucency required in reproducing the incised portion of natural tooth and the high strength applicable to long span bridges of 4 units or more.

Patent Document 4 discloses a preparing method of a zirconia blank for dental cutting and machining in which a zirconia raw material powder containing 5 mol % of yttrium is laminated on the incisal end portion side and a zirconia raw material powder containing 3 mol % of yttrium is laminated on the tooth cervical portion side. The zirconia perfect sintered body prepared from the zirconia blank for dental cutting and machining has translucency suitable for the incisal end portion, and high strength in the tooth cervical portion. However, since there is a difference in thermal expansion between the layers, the sintered body is deformed in a case of a long span bridge or the like, and therefore there is a problem that the fitness is deteriorated in the long span bridge.

Patent Document 5 discloses a zirconia blank for dental cutting and machining in which a zirconia raw material powder containing 6 to 10 mol % of yttrium is laminated on the incisal end portion side and a zirconia raw material powder containing 4.5 to 6 mol % of yttrium is laminated on the tooth cervical portion side, and a zirconia perfect sintered body prepared from the zirconia blank for dental cutting and machining. The sintered body has translucency suitable for the incisal end portion, and high strength in the tooth cervical portion which requires strength in a long span bridge. However, even in the sintered body, since there is a difference in thermal expansion between the layers, the sintered body is deformed in a case of a long span bridge or the like, and therefore there is a problem that the fitness is deteriorated in the long span bridge, breakage is easily caused in an incisal portion containing high yttrium content and the like.

As described above, in the conventional zirconia mill blank for dental cutting and machining, it has been impossible to provide a zirconia perfect sintered body which has a chroma of an excellent color tone and excellent translucency and does not cause deformation has been required, while maintaining high strength.

Moreover, in the prosthetic device prepared by cutting and machining, the same transparency as a whole is not required. In particular, like the natural tooth, while transparent is particularly required in the tip of the enamel, on the other hand, in the cervical portion, there is a case that an abutment tooth on which the prosthetic device is placed may be a discolored tooth or metal, and therefore transparent is not required conversely in order not to adversely affect the color tone of the prosthetic device. In other words, if the transparency in the cervical portion is too high, the crown color may not have the desired color tone, and therefore, a preparation of an aesthetic prosthetic device in which transparency is high in only the enamel part while the transparency decreases as it moves to the cervical portion has been required.

In order to solve these problems, various liquids have been applied to a zirconia mill blank for dental cutting and machining or a zirconia perfect sintered body for imparting a color reproduction similar to that of the natural tooth, to the zirconia perfect sintered body.

For example, Patent Document 6 discloses a method of adjusting the color of a prosthetic device in which a prosthetic device is prepared by cutting and machining a pres-intered zirconia for dental cutting and the prosthetic device is applied with a metal ion or a metal complex solution and thereafter is sintered. Although this method reproduces the color tone of tooth in the prosthetic device prepared by cutting and machining the pre-sintered zirconia for dental cutting, it has not been possible to improve the transparency and the chroma.

Patent Document 7 discloses a technique for facilitating the infiltration of a coloring liquid into a pre-sintered zirconia for dental cutting by defining the range of the BET specific surface area of the zirconia. However, even with this method, it has not been possible to improve the transparency and the chroma of the surface of the prosthetic device prepared by cutting and machining.

Patent Document 8 discloses a technique of a solution for coloring a pre-sintered zirconia for dental cutting. In this document, it is described that since this technique does not use water as a solvent, it is possible to reduce the contamination of the baking furnace with an acid or the like and to exhibit an excellent color develop property. However, although this method has the coloring property of the prosthetic device, it has not been able to improve the transparency and the chroma of the surface layer.

Although Patent Documents 5 to 8 disclose a technique for improving the transparency of a zirconia prosthetic device which is cut and machined by the dental CAD/CAM system and a technique for coloring the same, these prior arts cannot improve transparency without reducing the strength of the zirconia prosthetic device having high strength. Therefore, a zirconia perfect sintered body which has a chroma of an excellent color tone and excellent translucency and does not cause deformation has been required, while maintaining high strength.

CITATION LIST

Patent Literature

Patent Document 1: Japanese Unexamined Patent Application Publication No. JPS 60-235762 A
Patent Document 2: Japanese Patent No. JP5608976 B
Patent Document 3: International Publication WO2015/199018 A1
Patent Document 4: US Unexamined Patent Application Publication No. US2016/0354186 A1
Patent Document 5: US Unexamined Patent Application Publication No. U52017/0245970 A1
Patent Document 6: Japanese Unexamined Patent Application Publication (Translation of PCT Application) No. JP2002-536280 A1
Patent Document 7: Japanese Unexamined Patent Application Publication (Translation of PCT Application) No. JP2015-536904 A1
Patent Document 8: Japanese Unexamined Patent Application Publication (Translation of PCT Application) No. JP2013-529599 A1

SUMMARY OF INVENTION

Technical Problem

An object of the present invention is to provide a zirconia perfect sintered body which has a chroma of an excellent color tone and excellent translucency as compared with a zirconia mill blank for dental cutting and machining prepared from a zirconia raw material powder containing various stabilizing materials while maintaining high strength, and does not cause deformation.

Solution to Problem

In order to solve the above problems, the present inventors have intensively studied a zirconia mill blank for dental cutting and machining which can provide a zirconia perfect sintered body which has a chroma of an excellent color tone and excellent translucency as compared with a conventional zirconia mill blank for dental cutting and machining prepared from a zirconia raw material powder containing various stabilizing materials. As a result, it was found that when a specific amount of a water-soluble compound salt which contains calcium, magnesium or a rare earth element such as yttrium and lanthanum and is not an oxide is contained in a zirconia mill blank for dental cutting and machining together with a stabilizing material consisting of a specific amount of oxide, a zirconia perfect sintered body which has a chroma of an excellent color tone and excellent translucency as compared with a conventional zirconia mill blank for dental cutting and machining prepared from a zirconia raw material powder containing various stabilizing materials and does not cause deformation, while maintaining high strength can be prepared from the zirconia mill blank for dental cutting and machining by perfect sintering. The present invention is based on the above findings.

The present invention is as follows.

The present invention provides a zirconia mill blank for dental cutting and machining for preparing a prosthesis device by cutting and machining, wherein: the zirconia mill blank for dental cutting and machining is a semi-fired zirconia mill blank for dental cutting and machining containing a semi-fired body of a ceramic particle, the zirconia mill blank for dental cutting and machining contains zirconium oxide, a stabilizing material consisting of an oxide, and a water-soluble compound salt which contains at least one element selected from calcium, magnesium and a rare earth element and is not an oxide, the content of the stabilizing material in terms of the oxide in the semi-fired body of the ceramic particle is within a range of 2 to 7 mol %, and the content of the water-soluble compound salt in the zirconia mill blank for dental cutting and machining is within a range of 0.1 to 3.5 mol %. In the zirconia mill blank for dental cutting and machining according to the present invention, it is preferable that the zirconia mill blank for dental cutting and machining consist of zirconium oxide, a stabilizing material consisting of an oxide, and a water-soluble compound salt.

In the zirconia mill blank for dental cutting and machining of the present invention, it is preferable that the water-soluble compound salt contains yttrium.

In the zirconia mill blank for dental cutting and machining of the present invention, it is preferable that the semi-fired body of the ceramic particle contains the zirconium oxide and the stabilizing material consisting of the oxide, and the water-soluble compound salt is supported on a surface of the semi-fired body of the ceramic particle.

In the zirconia mill blank for dental cutting and machining of the present invention in this case, it is preferable that a content of the water-soluble compound salt in a position spaced from a surface of the zirconia mill blank for dental cutting and machining by 45 to 55% of a dimension between the surface of the zirconia mill blank for dental cutting and machining and the center of gravity of the zirconia mill blank for dental cutting and machining in a direction from the surface toward the center of gravity of the zirconia mill blank for dental cutting and machining is within a range of 50 to 150% of a content of the water-soluble compound salt in a position spaced from the surface of the zirconia mill blank for dental cutting and machining by 10 to 20% of the dimension between the surface of the zirconia mill blank for dental cutting and machining and the center of gravity of the zirconia mill blank for dental cutting and machining.

In the zirconia mill blank for dental cutting and machining of the present invention, it is preferable that the semi-fired body of the ceramic particle contains the zirconium oxide, the stabilizing material consisting of the oxide and the water-soluble compound salt.

In the zirconia mill blank for dental cutting and machining of the present invention, it is preferable that the zirconia mill blank for dental cutting and machining contains Pr, Er, Fe, Co, Ni, Mn or Cu as a coloring material.

In this case, it is preferable in the zirconia mill blank for dental cutting and machining of the present invention that the zirconia mill blank for dental cutting and machining consists of a plurality of layers having different contents of the stabilizing material consisting of the oxide and/or the coloring material.

In the zirconia mill blank for dental cutting and machining of the present invention, it is preferable that the zirconia mill blank for dental cutting and machining has a disk shape or a block shape.

The present invention also provides a dental prosthetic device prepared from the zirconia mill blank for dental cutting and machining of the present invention.

The present invention also provides a preparing method of a preparing method of a zirconia mill blank for dental cutting and machining, comprising the following steps (1) and/or (2);

(1) semi-firing a ceramic particle containing zirconium oxide, 2 to 7 mol % of a stabilizing material consisting of an oxide, and 0.1 to 3.5 mol % of a water-soluble compound salt which contains at least one element selected from calcium, magnesium and a rare earth element and is not an oxide.

(2) semi-firing a ceramic particle containing zirconium oxide and 2 to 7 mol % of a stabilizing material consisting of an oxide, and impregnating the zirconia mill blank for dental cutting and machining containing the semi-fired ceramic particle with a solution of a water-soluble compound salt which contains at least one element selected from calcium, magnesium and a rare earth element and is not an oxide.

When the preparing method of the zirconia mill blank for dental cutting and machining of the present invention including the above step (2), it is preferable that the zirconia mill blank for dental cutting and machining containing the semi-fired ceramic particle is dried after impregnating with the solution of the water-soluble compound salt.

When the preparing method of the zirconia mill blank for dental cutting and machining of the present invention including the above step (2), it is preferable that the solution of the water-soluble compound salt contains a water-soluble cerium compound.

When the preparing method of the zirconia mill blank for dental cutting and machining of the present invention including the above step (2), it is preferable that the solution of the water-soluble compound salt contains a water-soluble cerium compound, a vegetable oil, and an organic solvent.

The present invention also provides a preparing method of a dental prosthetic device for preparing a dental prosthetic device from the zirconia mill blank for dental cutting and machining which is prepared by the preparing method of the zirconia mill blank for dental cutting and machining including the above step (2), comprising; dry cutting the zirconia mill blank for dental cutting and machining into the shape of a dental prosthetic device, and main firing the zirconia mill blank for dental cutting and machining having the shape of a dental prosthetic device.

The present invention also provides a preparing method of a dental prosthetic device for preparing a dental prosthetic device from the zirconia mill blank for dental cutting and machining which is prepared by the preparing method of the zirconia mill blank for dental cutting and machining including the above step (1), comprising; cutting the zirconia mill blank for dental cutting and machining into the shape of a dental prosthetic device, and main firing the zirconia mill blank for dental cutting and machining having the shape of a dental prosthetic device.

The present invention is also provides a transparency improving liquid containing the solution of the water-soluble compound salt for preparing the zirconia mill blank for dental cutting and machining or for preparing the dental prosthetic device of the present invention, comprising; a (a)

solution of the water-soluble compound salt that is not an oxide (excluding the cerium compound): 10 to 80 wt. %, and a (b) water: 20 to 90.

The present invention is also provides a transparency improving liquid containing the solution of the water-soluble compound salt for preparing the zirconia mill blank for dental cutting and machining or for preparing the dental prosthetic device of the present invention, comprising; a (a) solution of the water-soluble compound salt that is not an oxide (excluding the cerium compound): 10 to 80 wt. %, a (b) water: 8 to 86, and a (c) water-soluble cerium compound: 2 to 80 wt. %.

The present invention is also provides a transparency improving liquid containing the solution of the water-soluble compound salt for preparing the zirconia mill blank for dental cutting and machining or for preparing the dental prosthetic device of the present invention, comprising; a (a) solution of the water-soluble compound salt that is not an oxide (excluding the cerium compound): 10 to 80 wt. %, a (b) water and/or vegetable oil: 8 to 86, a (c) water-soluble cerium compound: 2 to 80 wt. %, and a (d) water-soluble organic solvent: 0.1 to 20 wt. %.

In this case, it is preferable in the transparency improving liquid of the present invention that the water-soluble organic solvent (d) is any one of alcohols, polyols and glycol ethers.

In this case, it is preferable in the transparency improving liquid of the present invention that the total content of the water-soluble compound salt that is not an oxide (excluding the cerium compound) (a) and the water-soluble cerium compound (c) is within a range of 30 to 70 wt. %.

The present invention is also provides a using method of the transparency improving liquid of the present invention, comprising; applying the transparency improving liquid to the zirconia mill blank for dental cutting and machining or immersing the zirconia mill blank for dental cutting and machining in the transparency improving liquid, to support the water-soluble compound salt that is not an oxide on a surface of the semi-fired body of the ceramic particle.

In the using method of the transparency improving liquid of the present invention, it is preferable that the zirconia mill blank for dental cutting and machining contains iron.

In the using method of the transparency improving liquid of the present invention, it is preferable that the zirconia mill blank for dental cutting and machining contains yttrium and/or erbium.

In this case, it is preferable in the using method of the transparency improving liquid of the present invention that a molar concentration of yttrium and/or erbium in the zirconia mill blank for dental cutting and machining is 4 mol % or less.

In the using method of the transparency improving liquid of the present invention, it is preferable that the transparency improving liquid is applied only on a surface layer of the dental prosthetic device cut from the zirconia mill blank for dental cutting and machining.

In this case, it is preferable in the using method of the transparency improving liquid of the present invention, the dental prosthetic device is an inlay, a laminate, a crown, or a bridge.

Advantageous Effects of Invention

According to the present invention, a zirconia perfect sintered body which has a chroma of an excellent color tone and excellent translucency as compared with a zirconia mill blank for dental cutting and machining prepared from a zirconia raw material powder containing various stabilizing materials while maintaining high strength, and does not cause deformation can be provided.

DESCRIPTION OF EMBODIMENTS

Hereinafter, specific embodiments of the present invention will be described in detail.

A zirconia mill blank for dental cutting and machining according to the present invention is a zirconia mill blank for dental cutting and machining for preparing a prosthetic device by cutting and machining. This zirconia mill blank for dental cutting and machining is a semi-fired zirconia mill blank for dental cutting and machining containing a semi-fired body (calcined body, or pre-sintered body) of a ceramic particle, and the zirconia mill blank for dental cutting and machining contains zirconium oxide, a stabilizing material consisting of an oxide (hereinafter, also referred to as "stabilizing material" simply in this specification), and a water-soluble compound salt which contains at least one element selected from calcium, magnesium and a rare earth element and is not an oxide (hereinafter, also simply referred to as "water-soluble compound salt" simply in this specification), the amount of the stabilizing material in the semi-fired body of the ceramic particle is within a range of 2 to 7 mol %, and the amount of the water-soluble compound salt in the zirconia mill blank for dental cutting and machining is within a range of 0.1 to 3.5 mol %. In the present invention, the prosthetic device is prepared by cutting and machining a zirconia mill blank for dental cutting and machining, and includes both a semi-fired body and a perfect sintered body. In this case, the zirconia mill blank for dental cutting and machining contains 89.5 to 97.9 mol % of zirconium oxide.

The zirconia mill blank for dental cutting and machining according to the present invention can be prepared by using a known zirconia raw material powder. Specifically, for example, the zirconia mill blank for dental cutting and machining according to the present invention can be prepared from a zirconia raw material powder containing a stabilizing material. Furthermore, it is preferable that the stabilizing material contained in the zirconia mill blank for dental cutting and machining contains yttrium and/or erbium.

In the zirconia mill blank for dental cutting and machining according to the present invention, the content of the stabilizing material in the semi-fired ceramic particles contained in the zirconia mill blank for dental cutting and machining is within a range of 2 to 7 mol %. In other words, in the present invention, 2 to 7 mol % of the semi-fired body of the ceramic particles consists of a stabilizing material consisting of an oxide. When the content of the stabilizing material consisting of an oxide in the semi-fired body of the ceramic particles is lower than 2 mol %, it is impossible to impart sufficient translucency to the zirconia perfect sintered body. On the other hand, when the content of the stabilizing material consisting of an oxide in the semi-fired body of the ceramic particles exceeds 7 mol %, it is difficult to impart sufficient strength, although the translucency of the zirconia perfect sintered body is improved. In the present invention, the content of the stabilizing material refers to a value expressed by mol % of the molar ratio of (stabilizing material content)/(the content of all inorganic oxide contained in the semi-fired body of the ceramic particles).

In the zirconia mill blank for dental cutting and machining according to the present invention, the content of the water-soluble compound salt in the zirconia mill blank for dental cutting and machining is within a range of 0.1 to 3.5 mol %.

In other words, in the present invention, 0.1 to 3.5 mol % of the zirconia mill blank for dental cutting and machining consists of a water-soluble compound salt. Preferably, the content of the water-soluble compound salt is within a range of 0.5 to 3.0 mol %. In the present invention, the content of the water-soluble compound salt refers to a value expressed by mol % of the molar ratio of (water-soluble compound salt content)/(the content of all inorganic oxide contained in the zirconia mill blank for dental cutting and machining).

When the content of the water-soluble compound salt in the zirconia mill blank for dental cutting and machining of the present invention is less than 0.1 mol %, it is impossible to impart sufficient translucency to the zirconia mill blank for dental cutting and machining. On the other hand, when the content exceeds 3.5 mol %, although the translucency of the zirconia perfect sintered body is improved, it is difficult to impart sufficient strength. In the present invention, the water-soluble compound salt preferably contains yttria. When the water-soluble compound salt contains yttria, the translucency can be further improved.

The zirconia mill blank for dental cutting and machining according to the present invention is preferably prepared by using a colored zirconia raw material powder. Specific examples include yellow zirconia raw material powder containing iron, red zirconia raw material powder containing erbium as a stabilizing material, and the like. In addition to these colored zirconia raw material powders, there is no problem even if a colored zirconia raw material powder containing element such as praseodymium, cobalt, nickel, manganese, chromium and copper is used in combination for a color tone adjustment. By containing these coloring materials, it is possible to approximate to the color tone of the natural tooth. In addition, for the purpose of improving the sinterability and suppressing low temperature deterioration, it is preferable to prepare by using a zirconia raw material powder containing 0.01 to 0.15 mol % of alumina (aluminum oxide) which is a sintering aid. When the zirconia raw material powder containing excessive alumina is used, the translucency of the zirconia perfect sintered body is lowered.

The preparing method of the zirconia mill blank for dental cutting and machining according to the present invention is not particularly limited, and can be prepared by, for example, a known preparing method. Specifically, it can be prepared by molding the zirconia raw material powder by a press molding. Furthermore, it can be prepared by a multi-layer molding in which zirconia raw material powders having different compositions, in particular, different stabilizing material and/or coloring material contents is press-molded in multiple stages. Further, the zirconia mill blank for dental cutting and machining according to the present invention is preferably subjected to CIP (cold isostatic pressing) treatment after the press molding. Further, the zirconia mill blank for dental cutting and machining according to the present invention may be, for example, semi-fired (calcined/pre-sintered) at 800 to 1200° C. in order to adjust the hardness to be suitable for cutting and machining.

Next, a first embodiment of the zirconia mill blank for dental cutting and machining according to the present invention will be described. In the zirconia mill blank for dental cutting and machining according to the first embodiment, the semi-fired body of the ceramic particles includes zirconium oxide and a stabilizing material consisting of an oxide, and a water-soluble compound salt is supported on the surface of the semi-fired body of the ceramic particles. The zirconia mill blank for dental cutting and machining according to the first embodiment substantially consists of the semi-fired body of the ceramic particles.

Such zirconia mill blank for dental cutting and machining can be prepared, for example, by semi-firing ceramic particles containing zirconium oxide and 2 to 7 mol % of a stabilizing material consisting of an oxide as a zirconia raw material powder, and impregnating the zirconia mill blank for dental cutting and machining containing the semi-fired ceramic particles with a solution of a water-soluble compound salt that contains at least one element selected from calcium, magnesium and a rare earth element and is not an oxide. In this case, the ceramic particles contain 93 to 98 mol % of zirconium oxide. More specifically, the zirconia mill blank for dental cutting and machining containing semi-fired ceramic particles is immersed in a solution of a water-soluble compound salt containing a water-soluble compound salt and water and preferably dried to support the water-soluble compound salt on the surface of the semi-fired ceramic particles contained in the zirconia mill blank for dental cutting and machining. In the present specification, "surface of the ceramic particle" means not only the outer surface of the ceramic particle but also the inner surface of the ceramic particle communicating with the outer surface of the ceramic particle. According to such preparation method, unlike the conventional zirconia mill blank for dental cutting and machining prepared from a zirconia raw material powder containing a predetermined amount of a stabilizing material in advance, the zirconia mill blank for dental cutting and machining may be added with an arbitrary amount of a water-soluble compound salt after semi-firing of the ceramic particles, in the zirconia mill blank for dental cutting and machining of the present invention. Therefore, the zirconia perfect sintered body prepared from the zirconia mill blank for dental cutting and machining prepared in this way can be imparted with the characteristic which has a chroma of an excellent color tone and excellent translucency as compared with a conventional zirconia mill blank for dental cutting and machining while maintaining high strength, and does not cause deformation.

In the zirconia mill blank for dental cutting and machining of the first embodiment, it is important that the solution of the water-soluble compound salt infiltrates into the inside and the water-soluble compound salt is supported. In order to achieve these, the relative density and the specific surface area of the zirconia mill blank for dental cutting and machining containing the semi-firing ceramic particles are important.

It is preferable that the relative density of the zirconia mill blank for dental cutting and machining of the first embodiment is within a range of 50 to 70%. When the relative density is less than 50%, a sufficient amount of the water-soluble compound salt may be not supported. Therefore, in this case, when the mill blank is sintered, preferable transparency may not be obtained and thus it is not preferable. On the other hand, when the relative density exceeds 70%, the solution of the water-soluble compound salt may not sufficiently infiltrate. Therefore, in this case, when the mill blank is sintered, preferable transparency may not be obtained and thus it is not preferable. In the present specifications, the relative density of the zirconia mill blank for dental cutting and machining means an apparent density of the zirconia mill blank for dental cutting and machining which is a semi-sintered body when the density of the perfect sintered body is 100%.

It is preferable that the specific surface area of the zirconia mill blank for dental cutting and machining of the first embodiment is within a range of 0.5 to 10 cm$^2$/g. When the specific surface area is less than 0.5 cm²/g, a sufficient amount of the water-soluble compound salt may be not supported. Therefore, in this case, when the mill blank is sintered (perfect-sintered), transparency may not be obtained and thus it is not preferable. On the other hand, when the specific surface area exceeds 10 cm²/g, the supported amount of the water-soluble compound salt is excessive. Therefore, in this case, sufficient transparency may not be obtained after sintering the zirconia mill blank for dental cutting and machining and thus it is not preferable.

The solution of the water-soluble compound salt used in the first embodiment is prepared by dissolving a water-soluble compound, which is not an oxide, of at least one element selected from calcium, magnesium, and a rare earth element such as yttrium and lanthanum. Among these, it is preferable to use a water-soluble compound of yttrium, calcium, magnesium or lanthanum consisting of any of a halogen compound, a nitrate, a sulfate and an organic acid salt. Specific examples thereof include yttrium chloride, calcium chloride, magnesium chloride, lanthanum chloride, yttrium nitrate, calcium nitrate, magnesium nitrate, lanthanum nitrate, yttrium acetate, yttrium carboxylate, calcium acetate, magnesium acetate, yttrium sulfate, calcium sulfate and magnesium sulfate. Among these, it is particularly preferable to use a water-soluble compound of an organic acid salt from the viewpoint of suppressing the contamination of the firing furnace and the like. Specific examples include yttrium acetate, yttrium carboxylate, calcium acetate, and magnesium acetate. These water-soluble compound salts of at least one element selected from calcium, magnesium and a rare earth element such as yttrium and lanthanum may be used alone or in combination of two or more thereof.

In the solution of the water-soluble compound salt used in the first embodiment, a content of the water-soluble compound salt is preferably within a range of 1 to 50 wt. %, more preferably 5 to 30 wt. %.

In the solution of the water-soluble compound salt used in the first embodiment, when the content of the water-soluble compound is less than 1 wt. %, because a sufficient water-soluble compound salt cannot be supported on the zirconia mill blank for dental cutting and machining, it is not preferable. On the other hand, when the content exceeds 50 wt. %, because the solubility of the water-soluble compound salt is deteriorated, it is not preferable.

A preparation method of the solution of the water-soluble compound salt used in the first embodiment is not particularly limited, and any methods can be used without any problems as long as the water-soluble compound is dissolved in water.

In the present invention, the solution of the water-soluble compound salt may contain a water-soluble cerium compound. Alternatively, the solution of the water-soluble compound salt may contain a water-soluble cerium compound, a vegetable oil and a water-soluble organic solvent.

The method for immersing the zirconia mill blank for dental cutting and machining according to the first embodiment in the solution of the water-soluble compound salt is not particularly limited as long as the solution of the water-soluble compound salt can infiltrate into the gap of the semi-fired ceramic particles contained in the zirconia mill blank for dental cutting and machining. In a simple and preferable method, the whole and/or a part of the zirconia mill blank for dental cutting and machining which includes the semi-fired ceramic particles is immersed in the solution of the water-soluble compound salt. When the whole and/or a part of the zirconia mill blank for dental cutting and machining which includes the semi-fired ceramic particles is immersed in the solution of the water-soluble compound salt, the solution of the water-soluble compound salt can gradually infiltrate by the capillarity into a space inside of the zirconia mill blank for dental cutting and machining, which communicating with the outside of the zirconia mill blank for dental cutting and machining.

As a specific method for immersing the zirconia mill blank for dental cutting and machining according to the first embodiment in the solution of the water-soluble compound salt, 1 to 100% of the total volume of the zirconia mill blank for dental cutting and machining which includes the semi-fired ceramic particles is preferably immersed in the solution of the water-soluble compound salt, and 10 to 100% is more preferably immersed. By controlling the immersion volume of the zirconia mill blank for dental cutting and machining which includes the semi-fired ceramic particles in the solution of the water-soluble compound salt, the water-soluble compound salt can be supported only in an arbitrary part of the zirconia mill blank for dental cutting and machining.

A specific atmosphere in which the zirconia mill blank for dental cutting and machining according to the first embodiment is immersed in the solution of the water-soluble compound salt is not particularly limited, and can be any of a normal pressure atmosphere, a reduced pressure atmosphere and a pressurized atmosphere without any problems. From the viewpoint of shortening the preparation time, the surrounding environment is in a reduced pressure atmosphere or a pressurized atmosphere in a preferable means because the infiltration of the solution of the water-soluble compound salt is promoted. In addition, it is effective for shortening the time of the step in which the solution of the water-soluble compound salt infiltrates into a space inside of the zirconia mill blank for dental cutting and machining, which communicating with the outside of the zirconia mill blank for dental cutting and machining, to repeat multiple times the operation of returning to normal pressure after the pressure reduction operation (pressure reduction/normal pressure operation) or the operation of returning to normal pressure after the pressuring operation (pressuring/normal pressure operation).

The time for immersing the zirconia mill blank for dental cutting and machining which includes the semi-fired ceramic particles in the solution of the water-soluble compound salt is not determined unconditionally and can be adjusted appropriately based on the relative density and the molded body size of the zirconia mill blank for dental cutting and machining which includes the semi-fired ceramic particles, and the degree of infiltration and the method for immersing of the solution of the water-soluble compound salt solution and the like. For example, the time for immersing is usually 1 to 120 hours in the case of immersing, the time for immersing is usually 0.5 to 12 hours in the case of immersing under reduced pressure, and the time for immersing is usually 0.2 to 6 hours in the case of contacting under pressurization.

It is preferable to take out the zirconia mill blank for dental cutting and machining from the solution of the water-soluble compound salt and to perform a drying step of the solution of the water-soluble compound salt after the solution of the water-soluble compound salt infiltrates into a space inside of the zirconia mill blank for dental cutting and machining, which communicating with the outside of the zirconia mill blank for dental cutting and machining. The drying step is not particularly limited, but a simple and preferable method is to dry under a normal pressure atmosphere. The drying temperature is not particularly limited, but is preferably within a range of 100 to 500° C., and more preferably within a range of 100 to 300° C. The drying time is not particularly limited, but is usually within a range of 1 to 12 hours.

The zirconia mill blank for dental cutting and machining according to the first embodiment prepared as described above is severed, cut, and polished so as to have a desired size as necessary, and is shipped as a product. In the zirconia mill blank for dental cutting and machining according to the first embodiment, the drying step is performed after the immersion of the solution of the water-soluble compound salt. Therefore, the zirconia mill blank for dental cutting and machining according to the first embodiment can be cut into the shape of a dental prosthetic device by dry cutting, and then main-fired (perfect sintered) to obtain a perfect sintered body.

The method for preparing a dental prosthetic device by perfect sintering the zirconia mill blank for dental cutting and machining according to the first embodiment after cutting is not particularly limited, but a simple and preferred method is to firing at normal pressure. The firing temperature is not particularly limited, but is preferably within a range of 1400 to 1650° C., and more preferably within a range of 1450 to 1600° C. The holding time at the maximum firing temperature is not particularly limited, but is preferably within a range of 2 to 12 hours, and more preferably within a range of 2 to 4 hours. The temperature increase rate is not particularly limited, but is preferably within a range of 1 to 400° C./min, and more preferably within a range of 3 to 100° C./min.

The zirconia mill blank for dental cutting and machining according to the first embodiment may provide a zirconia perfect sintered body which has a chroma of an excellent color tone and excellent translucency as compared with a zirconia mill blank for dental cutting and machining prepared from a conventional zirconia raw material powder while maintaining high strength, and does not cause deformation. Although these reasons are not clear, it is considered that because the water-soluble compound salt that can be solid-solved in zirconia is supported on the outermost surface of the zirconia mill blank for dental cutting and machining, the supported water-soluble compound salt is segregated in the vicinity of the grain boundary in the post-sintering process, and then promotes the phase transition of the crystal phase (from tetragonal to cubic) in the vicinity of the grain boundary to improve the translucency. Furthermore, it is considered that supporting a water-soluble compound salt that can be solid-solved in zirconia on the outermost surface of the zirconia mill blank for dental cutting and machining also provides an effect of reducing microcracks in the sintered body to improve the strength of the zirconia perfect sintered body.

In the zirconia mill blank for dental cutting and machining according to the first embodiment, it is preferable, in a direction from a surface of the zirconia mill blank for dental cutting and machining toward the center of gravity of the zirconia mill blank for dental cutting and machining, that the content of the water-soluble compound salt at the position of 45 to 55% of the dimension from the surface of the zirconia mill blank for dental cutting and machining to the center of gravity of the zirconia mill blank for dental cutting and machining is within a range of 50 to 150%, more preferably 70 to 130%, most preferably 90 to 110% of the content of the water-soluble compound salt at a position of 10 to 20% of the dimension from the surface of the zirconia mill blank for dental cutting and machining to the center of gravity of the zirconia mill blank for dental cutting and machining. That is, in a line segment from the surface of the zirconia mill blank for dental cutting and machining to the center of gravity of the zirconia mill blank for dental cutting and machining, the content of the water-soluble compound salt at a position of 45 to 55% of the dimension of the line segment from the surface is preferably 50 to 150% of the content of the water-soluble compound salt at a position of 10 to 20% of the dimension of the line segment from the surface. By satisfying such a relationship, it becomes possible to support the water-soluble compound salt uniformly over the entire outermost surface of the zirconia mill blank for dental cutting and machining, and therefore the effect of improving translucency and improving strength can be obtained uniformly throughout the entire zirconia perfect sintered body. The position of the surface in this case can be arbitrarily selected, and it is only necessary to satisfy the above relationship at any one of surface position. However, it is preferable that the above relationship is satisfied in a case that the position of the surface is a position where the dimension from the surface to the center of gravity of the zirconia mill blank for dental cutting and machining is minimized. When the zirconia mill blank for dental cutting and machining has a block shape, such a position of the surface is the center of one of the surfaces of the block. When the zirconia mill blank for dental cutting and machining has a disk shape, such a position of the surface is the center of a circular surface. The position of the surface in the above relationship may be a position where the dimension from the surface to the center of gravity of the zirconia mill blank for dental cutting and machining is maximized.

In the zirconia mill blank for dental cutting and machining according to the first embodiment, it is preferable to contain Pr, Er, Fe, Co, Ni or Cu as a coloring material. By containing these coloring materials, it is possible to more approximate to the color tone of the natural tooth.

In this case, it is preferable that the zirconia mill blank for dental cutting and machining according to the first embodiment consists of a plurality of layers having different contents of a stabilizing material and/or a coloring material. By adopting such a configuration, it is possible to further approximate to the color tone of the natural tooth.

The kind of a prosthesis device prepared by cutting and machining the zirconia mill blank for dental cutting and machining according to the first embodiment is not limited particularly, and there is no problem at all even if the prosthesis device is any of an inlay, a laminate, a crown, a bridge and the like. Therefore, a shape of a zirconia mill blank for dental cutting and machining which is cut and machined for preparing a prosthesis device is not limited particularly, and any zirconia mill blank for dental cutting and machining can be used even if the zirconia mill blank for dental cutting and machining has any shape such as a block shape corresponding to an inlay, a laminate, a crown and the like and a disk shape corresponding to a bridge.

Next, a second embodiment of the zirconia mill blank for dental cutting and machining according to the present invention will be described. In the zirconia mill blank for dental cutting and machining according to the second embodiment, the semi-fired body of the ceramic particles includes zirconium oxide, a stabilizing material consisting of an oxide and a water-soluble compound salt. The zirconia mill blank for dental cutting and machining according to the second embodiment substantially consists of a semi-fired body of the ceramic particles.

Such a zirconia mill blank for dental cutting and machining can be prepared, for example, by semi-firing ceramic particles containing zirconium oxide, 2 to 7 mol % of a stabilizing material consisting of an oxide, and 0.1 to 3.5 mol % of a water-soluble compound salt that contains at least one element selected from calcium, magnesium and a rare earth element and is not an oxide, as a zirconia raw material powder. In such prepared zirconia mill blank for dental cutting and machining, the stabilizing material and the water-soluble compound salt are contained in the zirconia mill blank for dental cutting and machining in a state where the stabilizing material and the water-soluble compound salt are entirely covered with the semi-fired ceramic particles. Therefore, in the zirconia mill blank for dental cutting and machining according to the second embodiment, the water-soluble compound salt is not supported on the surface of the semi-fired ceramic particles. The zirconia perfect sintered body prepared from the zirconia mill blank for dental cutting and machining prepared in this way can be imparted with the characteristic which has a chroma of an excellent color tone and excellent translucency as compared with a conventional zirconia mill blank for dental cutting and machining while maintaining high strength, and does not cause deformation because sufficient stabilizing material and water-soluble compound salt are contained.

With respect to the relative density and specific surface area of the zirconia mill blank for dental cutting and machining according to the second embodiment, approximately the same relative density and specific surface area as those in the zirconia mill blank for dental cutting and machining according to the first embodiment can be used. In this case, it is possible to impregnate in a solution of a water-soluble compound salt as necessary, similarly to the zirconia mill blank for dental cutting and machining according to the first embodiment.

The water-soluble compound salt used in the second embodiment may be a water-soluble compound, which is not an oxide, of at least one element selected from calcium, magnesium and a rare earth element such as yttrium and lanthanum. Among these, it is preferable to use a compound of yttrium, calcium, magnesium or lanthanum consisting of any of a halogen compound, a nitrate, a sulfate and an organic acid salt. Specific examples thereof include yttrium chloride, calcium chloride, magnesium chloride, lanthanum chloride, yttrium nitrate, calcium nitrate, magnesium nitrate, lanthanum nitrate, yttrium acetate, yttrium carboxylate, calcium acetate, magnesium acetate, yttrium sulfate, calcium sulfate and magnesium sulfate. Among these, it is particularly preferable to use a water-soluble compound of an organic acid salt from the viewpoint of suppressing the contamination of the firing furnace and the like. Specific examples include yttrium acetate, yttrium carboxylate, calcium acetate, and magnesium acetate. These water-soluble compound salts of at least one element selected from calcium, magnesium and a rare earth element such as yttrium and lanthanum may be used alone or in combination of two or more thereof.

The zirconia mill blank for dental cutting and machining according to the second embodiment prepared as described above is also severed, cut, and polished so as to have a desired size as necessary, and is shipped as a product. The zirconia mill blank for dental cutting and machining according to the second embodiment can be cut into the shape of a dental prosthetic device, and then main-fired (perfect sintered) to obtain a perfect sintered body.

The zirconia mill blank for dental cutting and machining according to the second embodiment can be perfect sintered by the same method as the zirconia mill blank for dental cutting and machining according to the first embodiment to prepare a dental prosthetic device.

The zirconia mill blank for dental cutting and machining according to the second embodiment also may provide a zirconia perfect sintered body which has a chroma of an excellent color tone and excellent translucency as compared with a zirconia mill blank for dental cutting and machining prepared from a conventional zirconia raw material powder while maintaining high strength, and does not cause deformation.

It is also preferable that the zirconia mill blank for dental cutting and machining according to the second embodiment contains Pr, Er, Fe, Co, Ni or Cu as a coloring material. In this case, it is preferable that the zirconia mill blank for dental cutting and machining according to the second embodiment consists of a plurality of layers having different contents of a stabilizing material and/or a coloring material.

The kind of a prosthesis device prepared by cutting and machining the zirconia mill blank for dental cutting and machining according to the second embodiment is not limited particularly, and there is no problem at all even if the prosthesis device is any of an inlay, a laminate, a crown, a bridge and the like. Therefore, a shape of a zirconia mill blank for dental cutting and machining which is cut and machined for preparing a prosthesis device is not limited particularly, and any zirconia mill blank for dental cutting and machining can be used even if the zirconia mill blank for dental cutting and machining has any shape such as a block shape corresponding to an inlay, a laminate, a crown and the like and a disk shape corresponding to a bridge.

Next, the transparency improving liquid containing a solution of a water-soluble compound salt for preparing a zirconia mill blank for dental cutting and machining of the present invention will be described. This transparency improving liquid can also be used for preparing a dental prosthetic device. In the first embodiment of the transparency improving liquid of the present invention, the transparency improving liquid contains a solution of (a) water-soluble compound salt that is not an oxide (excluding a cerium compound): 10 to 80 wt. % and a (b) water: 20 to 90 wt. %. It is preferable that the transparency improving liquid of the first embodiment consists of the solution of (a) water-soluble compound salt that is not an oxide (excluding a cerium compound): 10 to 80 wt. % and the (b) water: 20 to 90 wt. %.

The component (a): water-soluble compound salt contained in the transparency improving liquid of the first embodiment is a water-soluble compound, which is not an oxide, of at least one element selected from calcium, magnesium and a rare earth element such as yttrium and lanthanum and the like (excluding a cerium compound). Any water-soluble compounds may be used regardless of the degree of the solubility as long as it dissolves in water. Among these, it is preferable to use a compound of yttrium, calcium, magnesium or a rare earth element such as lanthanum consisting of any of a halogen compound, a nitrate, a sulfate and an organic acid salt. Specific examples thereof include yttrium chloride, calcium chloride, magnesium chloride, lanthanum chloride, yttrium nitrate, calcium nitrate, magnesium nitrate, lanthanum nitrate, yttrium acetate, yttrium carboxylate, calcium acetate, magnesium acetate, yttrium sulfate, calcium sulfate and magnesium sulfate. Among these, yttrium chloride and yttrium nitrate are particularly preferable. In addition, it is particularly preferable to use a water-soluble compound of an organic acid salt from the viewpoint of suppressing the contamination of the firing furnace and the like. Specific examples include yttrium acetate, yttrium carboxylate, calcium acetate and magnesium acetate. These water-soluble compound salts of at least one element selected from calcium, magnesium and a rare earth element such as yttrium and lanthanum may be used alone or in combination of two or more thereof. It is essential that the content of the (a): water-soluble compound salt which is not an oxide is within a range of 10 to 80 wt. %, and the content is preferably within a range of 20 wt. % to 60 wt. %. When the content of the water-soluble compound salt contained in the transparency improving liquid is less than 10 wt. %, for example, the improvement in transparency is not recognized even if the transparency improving liquid is applied to a prosthesis device. On the other hand, when the content exceeds 80 wt. %, because the solubility to water decreases remarkably, it is impossible to prepare a uniform transparency improving liquid.

The water (b) contained in the transparency improving liquid of the first embodiment is necessary for dissolving or dispersing the water-soluble compound salt that is not an oxide (a). Although the water contained in the transparency improving liquid of the first embodiment is not particularly limited, but it is possible to use ion exchanged water, Japanese pharmacopeia purified water and Japanese pharmacopeia distilled water and the like. The content of water contained in the transparency improving liquid of the first embodiment is within a range of 20 to 90 wt. %, preferably within a range of 30 to 70 wt. %. When the content is little, the solubility of the water-soluble compound salt (a) decreases and when the content is large, the effect of the transparency improvement decreases.

The transparency improving liquid may contain a (c) water-soluble cerium compound: 2 to 80 wt. %. In this case, the (b) water is contained within a range of 8 to 86 wt. %. That is, in the second embodiment of the transparency improving liquid of the present invention, the transparency improving liquid contains a solution of a (a) water-soluble compound salt that is not an oxide (excluding a cerium compound): 10 to 80 wt. %, a (b) water: 8 to 86 wt. %, and a (c) water-soluble cerium compound: 2 to 80 wt. %.

As the component (c) water-soluble cerium compound contained in the transparency improving liquid of the second embodiment, any water-soluble cerium compounds may be used regardless of the degree of the solubility as long as it dissolves in water. Among them, it is preferable to use a water-soluble cerium compound consisting of any one of a halogen compound, a nitrate, a sulfate and an organic acid salt. Specific examples thereof include cerium chloride, cerium nitrate, cerium acetate, cerium sulfate and cerium carboxylate. Among these, it is particularly preferable that cerium chloride and/or cerium nitrate is used. These water-soluble cerium compounds may be used alone or in combination of two or more thereof. It is essential that the content of the water-soluble cerium compound contained in the transparency improving liquid of the second embodiment is within a range of 2 to 80 wt. %, and the content is preferably within a range of 2 wt. % to 40 wt. %. When the content of the water-soluble cerium compound contained in the transparency improving liquid is less than 2 wt. %, for example, the improvement in transparency is not recognized even if the transparency improving liquid is applied to a prosthesis device. On the other hand, when the content is more than 80 wt. %, because the solubility to water decreases remarkably, it is impossible to prepare a uniform transparency improving liquid.

The water-soluble compound salt that is not an oxide (a) contained in the transparency improving liquid of the second embodiment may be the same as that of the first embodiment and may be used in the same amount as that of the first embodiment. The water (b) contained in the transparency improving liquid of the second embodiment is necessary for dissolving or dispersing the water-soluble compound salt that is not an oxide (a) and the water-soluble cerium compound (c) and may be the same as that of the first embodiment. The content of water contained in the transparency improving liquid of the second embodiment is within a range of 8 to 86 wt. %, preferably within a range of 30 to 70 wt. %. When the content is little, the solubility of the water-soluble compound salt that is not an oxide (a) and the water-soluble cerium compound (c) decreases and when the content is large, the effect of the transparency improvement decreases.

In the transparency improving liquid of the second embodiment, it is preferable that the total content of the water-soluble compound salt that is not an oxide (a) and the water-soluble cerium compound (c) in the transparency improving liquid is within a range of 30 to 70 wt. %. When the content is less than 30 wt. %, insufficient improvement in transparency may easily occur, and when the content exceeds 70 wt. %, the viscosity increases, therefore, a deterioration of the permeability to the prosthetic device in case of applying the transparency improving liquid to the prosthetic device may easily occur, for example.

The transparency improving liquid may contain a (d) water-soluble organic solvent: 0.1 to 20 wt. %. In this case, the component (b) is water and/or vegetable oil. That is, in the third embodiment of the transparency improving liquid of the present invention, the transparency improving liquid contains a solution of a (a) water-soluble compound salt that is not an oxide (excluding a cerium compound): 10 to 80 wt. %, a (b) water and/or vegetable oil: 8 to 86 wt. %, a (c) water-soluble cerium compound: 2 to 80 wt. %, and a (d) water-soluble organic solvent: 0.1 to 20 wt. %.

As the water-soluble organic solvent (d) contained in the transparency improving liquid of the third embodiment, an organic solvent compatible with the water or a vegetable oil described later is appropriately selected and used. It is preferable that the water-soluble organic solvent acts as a thickener to adjust a viscosity and does not generate a residue as an organic matter in sintering the zirconia. Specific examples of the water-soluble organic solvent include alcohols, polyols, glycol ethers, more specifically methanol, ethanol, isopropanol, ethylene glycol, polyethylene glycol, acetone, 1,4-dioxane, polypropylene glycol. Among them, polyethylene glycol and polypropylene glycol are preferable. In addition, a content of the water-soluble organic solvent contained in the transparency improving liquid of the third embodiment is within a range of 0.1 to 20 wt. %. When the content is less than 0.1 wt. %, application property, for example in case of applying the transparency improving liquid to the prosthetic device, decreases. When the content exceeds 20 wt. %, a residue as an organic matter may be generated in sintering the zirconia.

The water-soluble compound salt that is not an oxide (a) contained in the transparency improving liquid of the third embodiment may be the same as that of the first embodiment and may be used in the same amount as that of the first embodiment. Further, the water-soluble cerium compound (c) contained in the transparency improving liquid of the third embodiment may be the same as that of the second embodiment and may be used in the same amount as that of the second embodiment. Furthermore, the water used as the component (b) of the third embodiment may be the same as that of the second embodiment and may be used in the same amount as that of the second embodiment. In the third embodiment, the component (b) consists of water and/or vegetable oil. The vegetable oil used in the transparency improving liquid of the third embodiment is not particularly limited, and any vegetable oil can be used. Specific examples include gum nene, pinene, D-limonene, terpineol and the like, and among them, pinene and D-limonene are preferable. The content of the vegetable oil contained in the transparency improving liquid of the third embodiment is within a range of 8 to 86 wt. %, and preferably within a range of 30 to 70 wt. %. When the content is little, the solubility of the water-soluble compound salt that is not an oxide (a) and the solubility of the water-soluble cerium compound (c) decrease and when the content is large, the effect of the transparency improvement decreases.

In the transparency improving liquid of the third embodiment, it is also preferable that the total content of the water-soluble compound salt (a) and the water-soluble cerium compound (c) in the transparency improving liquid is within a range of 30 to 70 wt. %. When the content is less than 30 wt. %, insufficient improvement in transparency may easily occur, and when the content exceeds 70 wt. %, the viscosity increases, therefore, a deterioration of the permeability to the prosthetic device in case of applying the transparency improving liquid to the prosthetic device may easily occur, for example.

The transparency improving liquid of the present invention may contain an organic marker which includes an organic dye as a base component. In such a manner, when the transparency improving liquid is applied to a prosthesis device prepared by cutting and machining a zirconia mill blank for dental cutting and machining, it is possible to visualize the applied area and to visualize the applied amount of the transparency improving liquid and the degree of infiltration thereof. It is required for the organic dye not to contain an inorganic matter. Specific examples of the organic dye include gardenia yellow pigment, annatto pigment and red cabbage pigment. Among them, red cabbage pigment and gardenia yellow pigment are preferable.

Next, a using method of the transparency improving liquid of the present invention will be described. The transparency improving liquid of the present invention is used for, for example, applying or immersing a zirconia mill blank for dental cutting and machining to support a water-soluble compound salt on the surface of the zirconia mill blank for dental cutting and machining. Specifically, it can be used as a water-soluble compound salt solution in which the zirconia mill blank for dental cutting and machining is immersed, in preparing the zirconia mill blank for dental cutting and machining according to the first embodiment described above. Further, after the preparation of the zirconia mill blank for dental cutting and machining according to the first and second embodiments described above, it can be used as a coating liquid which is applied to the prepared zirconia mill blank for dental cutting and machining or a dental prosthesis device prepared from these zirconia mill blank for dental cutting and machining.

In the using method of the transparency improving liquid of the present invention, it is preferable that the zirconia mill blank for dental cutting and machining to which the transparency improving liquid is applied or immersed contains iron.

It is preferable embodiment for providing a prosthetic device which has a chroma of an excellent color tone and excellent translucency while maintaining high strength, and does not cause deformation by applying the transparency improving liquid of the present invention to a zirconia mill blank for dental cutting and machining and a prosthetic device cut from the zirconia mill blank for dental cutting and machining, that the transparency improving liquid of the present invention is applied to a prosthetic device prepared by cutting and machining the zirconia mill blank for dental cutting and machining.

When the transparency improving liquid of the present invention is applied to a zirconia mill blank for dental cutting and machining and a prosthesis device (semi-sintered body) in preparing the prosthesis device by cutting and machining the zirconia mill blank for dental cutting and machining which is porous and pre-sintered and thereafter perfect sintering is performed, a chroma of a color tone and transparency in the perfect sintered body are improved by the transparency improving liquid of the present invention. That is, the transparency improving liquid of the present invention is applied to a zirconia mill blank for dental cutting and machining and a prosthesis device which are pre-sintered bodies to infiltrate from the surface to the inside thereof and improves the chroma of the color tone and the transparency in the perfect sintered body by perfect sintering thereafter. Therefore, the relative density, the specific surface area and the composition of a zirconia mill blank for dental cutting and machining which is cut and machined for preparing a prosthesis device affect them.

Accordingly, when the transparency improving liquid of the present invention is applied to a zirconia mill blank for dental cutting and machining which is cut and machined for preparing a prosthesis device, it is preferable that the relative density of the zirconia mill blank for dental cutting and machining is within a range of 45 to 60%. In the present specifications, the relative density of the zirconia mill blank for dental cutting and machining means an apparent density of the zirconia mill blank for dental cutting and machining which is a semi-sintered body when the density of the perfect sintered body is 100%. When the relative density is less than 45%, because the applied transparency improving liquid infiltrates too much into the inside, a strength of the prosthetic device may decrease. On the other hand, when the relative density exceeds 60%, there may be a problem that the applied transparency improving liquid is hard to infiltrate. In addition, it is preferable that the specific surface area of a zirconia mill blank for dental cutting and machining is within a range of 10 to 200 $cm^2/g$ from a point of view that a pre-sintered body is porous. When the specific surface area is less than 10 $cm^2/g$, there is a case where the infiltration of the applied transparency improving liquid is not sufficient, and when the specific surface area exceeds 200 $cm^2/g$, there is a case where a strength of the prosthetic device may decrease.

In addition, it is preferable embodiment that a zirconia mill blank for dental cutting and machining which is cut and machined for preparing a prosthesis device which is applied with the transparency improving liquid of the present invention contains yttrium and/or erbium as a stabilizing material. This affects the chroma of the color tone and the transparency in the prosthesis device applied with the transparency improving liquid of the present invention. It is preferable that the molar concentration of the stabilizing material contained in the zirconia mill blank for dental cutting and machining is 4 mol % or less. When the molar concentration of the stabilizing material in the zirconia mill blank for dental cutting and machining exceeds 4 mol %, there is a case in after perfect sintering although the transparency of the prosthetic device is improved, the decrease of the strength may occur.

The kind of a prosthesis device applied with the transparency improving liquid of the present invention is not limited particularly, and there is no problem at all even if the prosthesis device is any of an inlay, a laminate, a crown, a bridge and the like. Therefore, a shape of a zirconia mill blank for dental cutting and machining which is cut and machined for preparing a prosthesis device is not limited particularly, and any zirconia mill blank for dental cutting and machining can be used even if the zirconia mill blank for dental cutting and machining has any shape such as a block shape corresponding to an inlay, a laminate, a crown and the like and a disk shape corresponding to a bridge. In addition, it is more preferable embodiment that a zirconia mill blank for dental cutting and machining which has a multilayered structure and has a block shape or a disk shape is used for preparing more aesthetic prosthesis device by applying the transparency improving liquid of the present invention.

When the transparency improving liquid of the present invention is used as a coating liquid, it is preferable that the transparency improving liquid is prepared by mixing all components, and a liquid form which is in a state with the fluidity is preferable. The state of the transparency improving liquid is not limited particularly and specific examples of the state includes a state where all components are uniformly compatible with, a state where the opaque imparting liquid is divided into a plurality of layers and a state where a specific component is separated and precipitated. There is no problem particularly as long as the whole is in a uniform state by an operation such as shaking before use. Among them, a liquid form which has fluidity and low viscosity and in which all components are compatible with as described above is preferable from a point of view that the transparency improving liquid of the present invention infiltrates after applying the transparency improving liquid of the present invention to a prosthesis device.

Furthermore, with respect to an application method to a prosthetic device by using the transparency improving liquid of the present invention, there is no problem in any method as long as the surface of the prosthetic device is uniformly applied, and any application methods such as application by a brush, spraying using a spray, dropping using a pipette and the like can be used without any problem. Among these, it is preferable to apply using a brush or the like because it can be applied uniformly only to the surface of the prosthetic device.

When the transparency improving liquid of the present invention is used as a coating liquid, it is preferable to apply the transparency improving liquid only to the surface layer of a dental prosthetic device cut from a zirconia mill blank for dental cutting and machining. By doing this, it is possible to improve the transparency of only the surface layer in assuming the tooth crown form, for example, by applying only the enamel part of the tooth crown form, it is possible to maintain the cervical part in the opaque state.

Next, a method for preparing a zirconia mill blank for dental cutting and machining using the transparency improving liquid of the present invention will be described. When the transparency improving liquid of the present invention is used as a solution of a water-soluble compound salt in which a zirconia mill blank for dental cutting and machining is immersed, for example, ceramic particles containing zirconium oxide and 2 to 7 mol % of a stabilizing material consisting of an oxide as a zirconia raw material powder is prepared, a coloring material is contained in the ceramic particles, and the zirconia raw material powders having different contents of the coloring material are press-molded in a multistage manner to prepare a press-molded body having a multilayer structure. The press-molded body is subjected to CIP treatment, and then calcined (pre-sintered) at 800 to 1200° C. to prepare a semi-fired body. Next, 10 to 100% of the total volume of the semi-fired body is immersed in the solution of the water-soluble compound salt. The immersion can be performed, for example, under a normal pressure atmosphere for 1 to 120 hours, under a reduced pressure atmosphere for 0.5 to 12 hours, and under a pressurized atmosphere for 0.2 to 6 hours.

When the transparency improving liquid of the present invention is used as a coating liquid for a zirconia mill blank for dental cutting and machining, similarly to the case that the transparency improving liquid is used as the solution of the water-soluble compound salt in which the zirconia mill blank for dental cutting and machining is immersed, a zirconia mill blank for dental cutting and machining which is a semi-fired body is prepared. The transparency improving liquid of the present invention is applied to the zirconia mill blank for dental cutting and machining which is a semi-fired body, using a brush or the like.

Example

Hereinafter, the present invention is described by way of Examples in more detail, and specifically, but the present invention is not limited to these Examples.

[Preparation of Preliminary Bodies of Zirconia Mill Blank for Dental Cutting and Machining]

Preparation of Preliminary Body of Zirconia Mill Blank for Dental Cutting and Machining (A-1)

Zirconia raw powder containing 3.0 mol % of yttrium oxide (Zpex: manufactured by Tosoh Corporation, theory density: 6.092 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-1).

Preparation of Preliminary Body of Zirconia Mill Blank for Dental Cutting and Machining (A-2)

Zirconia raw powder containing 3.0 mol % of yttrium oxide (Zpex: manufactured by Tosoh Corporation, theory density: 6.092 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (800° C., 30 minutes) to prepare a preliminary body of zirconia mill blank for dental cutting and machining (A-2).

Preparation of Preliminary Body of Zirconia Mill Blank for Dental Cutting and Machining (A-3)

Zirconia raw powder containing 3.0 mol % of yttrium oxide (Zpex: manufactured by Tosoh Corporation, theory density: 6.092 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1200° C., 30 minutes) to prepare a preliminary body of zirconia mill blank for dental cutting and machining (A-3).

Preparation of Preliminary Body of Zirconia Mill Blank for Dental Cutting and Machining (A-4)

Zirconia raw powder containing 5.5 mol % of yttrium oxide (Zpex SMILE: manufactured by Tosoh Corporation, theory density: 6.050 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-4).
Preparation of Preliminary Body of Zirconia Mill Blank for Dental Cutting and Machining (A-5)

Zirconia raw powder containing 6.5 mol % of yttrium oxide (theory density: 6.035 g/cm$^3$) was filled in a mold ($\varphi$100 mm), and press molding was performed to obtain a molded body. Further, the molded body (surface pressure: 30 MPa) was subjected to CIP treatment (200 MPa, 1 minute). Thereafter, calcination was performed in an electric furnace (1000° C., 30 minutes) to prepare a preliminary body of zirconia mill blank for dental cutting and machining (A-5).
Preparation of Preliminary Body of Zirconia Mill Blank for Dental Cutting and Machining (A-6)

"SHOFU DISK ZR Lucent FA" which was prepared by laminating a colored zirconia raw material powder containing 5.5 mol % of yttrium (theory density: 6.050 g/cm$^3$) was used as a preliminary body of zirconia mill blank for dental cutting and machining (A-6).
Preparation of Preliminary Body of Zirconia Mill Blank for Dental Cutting and Machining (A-7)

Zirconia raw powder containing 2.0 mol % of yttrium oxide (theory density: 6.114 g/cm$^3$) was filled in a mold ($\varphi$100 mm), and press molding was performed to obtain a molded body. Further, the molded body (surface pressure: 30 MPa) was subjected to CIP treatment (200 MPa, 1 minute). Thereafter, calcination was performed in an electric furnace (1000° C., 30 minutes) to prepare a preliminary body of zirconia mill blank for dental cutting and machining (A-7).
Preparation of Preliminary Body of Zirconia Mill Blank for Dental Cutting and Machining (A-8)

Zirconia raw powder containing 7.0 mol % of yttrium oxide (theory density: 6.026 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-8).
Preparation of Preliminary Body of Zirconia Mill Blank for Dental Cutting and Machining (A-9)

Zirconia raw powder containing 3.0 mol % of yttrium oxide (Zpex: manufactured by Tosoh Corporation, theory density: 6.092 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (700° C., 30 minutes) to prepare a preliminary body of zirconia mill blank for dental cutting and machining (A-9).
Preparation of Preliminary Body of Zirconia Mill Blank for Dental Cutting and Machining (A-10)

Zirconia raw powder containing 3.0 mol % of yttrium oxide (Zpex: manufactured by Tosoh Corporation, theory density: 6.092 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1300° C., 30 minutes) to prepare a preliminary body of zirconia mill blank for dental cutting and machining (A-10).
Preparation of Preliminary Body of Zirconia Mill Blank for Dental Cutting and Machining (A-11)

Zirconia raw powder containing 3.0 mol % of yttrium oxide and 3.3 mol % of yttrium acetate (theory density: 6.050 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-11).
Preparation of Preliminary Body of Zirconia Mill Blank for Dental Cutting and Machining (A-12)

Zirconia raw powder containing 3.0 mol % of yttrium oxide and 1.0 mol % of yttrium acetate (theory density: 6.050 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-12).
Preparation of Preliminary Body of Zirconia Mill Blank for Dental Cutting and Machining (A-13)

Zirconia raw powder containing 8.0 mol % of yttrium oxide (theory density: 6.050 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1300° C., 30 minutes) to prepare a preliminary body of zirconia mill blank for dental cutting and machining (A-13).
Preparation of Preliminary Body of Zirconia Mill Blank for Dental Cutting and Machining (A-14)

Zirconia raw powder containing 1.0 mol % of yttrium oxide (theory density: 5.980 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1300° C., 30 minutes) to prepare a preliminary body of zirconia mill blank for dental cutting and machining (A-14).
Preparation of Preliminary Body of Zirconia Mill Blank for Dental Cutting and Machining (A-15)

Zirconia raw powder containing 6.3 mol % of yttrium oxide and 0.1 mol % of yttrium acetate (theory density: 6.050 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-15).
Preparation of Preliminary Body of Zirconia Mill Blank for Dental Cutting and Machining (A-16)

Zirconia raw powder containing 6.3 mol % of yttrium oxide and 0.5 mol % of yttrium acetate (theory density: 6.050 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-16).
Preparation of Preliminary Body of Zirconia Mill Blank for Dental Cutting and Machining (A-17)

Zirconia raw powder containing 6.3 mol % of yttrium oxide and 3.0 mol % of yttrium acetate (theory density: 6.050 g/cm$^3$) was filled in a mold ($\varphi$100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes)

to prepare a preliminary body of zirconia mill blank for dental cutting and machining (A-17).

Preparation of Preliminary Body of Zirconia Mill Blank for Dental Cutting and Machining (A-18)

Zirconia raw powder containing 6.3 mol % of yttrium oxide and 3.0 mol % of calcium acetate (theory density: 6.050 g/cm$^3$) was filled in a mold (φ100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-18).

Preparation of Preliminary Body of Zirconia Mill Blank for Dental Cutting and Machining (A-19)

Zirconia raw powder containing 6.3 mol % of yttrium oxide and 3.5 mol % of yttrium acetate (theory density: 6.050 g/cm$^3$) was filled in a mold (φ100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-19).

Preparation of Preliminary Body of Zirconia Mill Blank for Dental Cutting and Machining (A-20)

Zirconia raw powder containing 6.3 mol % of yttrium oxide and 4.0 mol % of yttrium acetate (theory density: 6.050 g/cm$^3$) was filled in a mold (φ100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-20).

Preparation of Preliminary Body of Zirconia Mill Blank for Dental Cutting and Machining (A-21)

Zirconia raw powder containing 3.0 mol % of yttrium oxide and 2.6 mol % of yttrium acetate (theory density: 6.050 g/cm$^3$) was filled in a mold (φ100 mm), and press molding (surface pressure: 30 MPa) was performed to obtain a molded body. Further, the molded body was subjected to CIP treatment (200 MPa, 1 minute). Thereafter, calcination was performed in an electric furnace (1000° C., 30 minutes) to prepare a preliminary body of zirconia mill blank for dental cutting and machining (A-21).

[Evaluation of Relative Density]

The test specimen for evaluating relative density was prepared by cutting and machining each preliminary body of zirconia mill blank for dental cutting and machining into a round plate shape (φ14 mm×1.6 mm). Diameter, height and weight of each test specimen was measured by using micro calipers, and each bulk density was measured. In addition, the density of the perfect sintered body prepared from each zirconia raw material powder was used as the theoretical density of each test specimen. The relative density was calculated by the following formula.

Relative density (%)=Bulk density of each specimen (g/cm$^3$)/Theoretical density (g/cm$^3$)×100

[Evaluation of Specific Surface Area]

The test specimen for evaluating specific surface area was prepared by cutting and machining each preliminary body of zirconia mill blank for dental cutting and machining into a cylindrical shape (φ4 mm×5 mm). BET specific surface area of each test specimen was measured by using an automatic specific surface area/micropore distribution measuring device (manufactured by Quantachrome Instruments).

Tables 1 to 3 show the composition and properties of preliminary body of zirconia mill blank for dental cutting and machining.

TABLE 1

|  | A-1 | A-2 | A-3 | A-4 | A-5 | A-6 | A-7 |
|---|---|---|---|---|---|---|---|
| Note | Single layer | Single layer | Single layer | Single layer | Single layer | 5 layers | Single layer |
| Contnent of stabilizing material (mol %) | 3 | 3 | 3 | 5.5 | 6.5 | 5.5 | 2 |
| Contnent of water-soluble compound salt (mol %) | 0 | 0 | 0 | 0 | 0 | 0 | 0 |
| Semi-firing temperature (° C.) | 1000 | 800 | 1200 | 1000 | 1000 | 1000 | 1000 |
| Relative density (%) | 53.7 | 51.9 | 61.5 | 52.9 | 54 | 53.1 | 53.1 |
| Specific surface area (m$^2$/g) | 7.4 | 9.5 | 0.5 | 6.3 | 7.1 | 6.5 | 4.5 |

TABLE 2

|  | A-8 | A-9 | A-10 | A-11 | A-12 | A-13 | A-14 |
|---|---|---|---|---|---|---|---|
| Note | Single layer | Single layer | Single layer | Single layer | Single layer | Single layer | Single layer |
| Contnent of stabilizing material (mol %) | 7 | 3 | 3 | 6.3 | 4 | 8 | 1 |
| Contnent of water-soluble compound salt (mol %) | 0 | 0 | 0 | 0 | 0 | 0 | 0 |
| Semi-firing temperature (° C.) | 1000 | 700 | 1300 | 1000 | 1000 | 1000 | 1000 |
| Relative density (%) | 55.2 | 47.4 | 75 | 54 | 53.5 | 52.3 | 51.5 |
| Specific surface area (m$^2$/g) | 4.1 | 9.6 | 0.2 | 5.8 | 6.7 | 8.8 | 5.8 |

TABLE 3

|  | A-15 | A-16 | A-17 | A-18 | A-19 | A-20 | A-21 |
|---|---|---|---|---|---|---|---|
| Note | Single layer | Single layer | Single layer | Single layer | Single layer | Single layer | Single layer |
| Contnent of stabilizing material (mol %) | 6.3 | 6.3 | 6.3 | 6.3 | 6.3 | 6.3 | 3 |
| Contnent of water-soluble compound salt (mol %) | 0.1 | 0.5 | 3 | 3 | 3.5 | 4 | 2.6 |

TABLE 3-continued

|  | A-15 | A-16 | A-17 | A-18 | A-19 | A-20 | A-21 |
|---|---|---|---|---|---|---|---|
| Semi-firing temperature (° C.) | 1000 | 700 | 1300 | 1000 | 1000 | 1000 | 1000 |
| Relative density (%) | 55.5 | 55.5 | 55.5 | 55.5 | 55.5 | 55.5 | 55.4 |
| Specific surface area (m²/g) | 5.8 | 5.9 | 5.9 | 5.9 | 6.1 | 6.2 | 6.1 |

Relative density: 55.4%, Specific surface area: 6.1 m²/g

[Preparation of Solution of Water-Soluble Compound Salt]

Tables 4 to 5 show the composition tables of solution of water-soluble compound salt. The solution of water-soluble compound salt was prepared by adding each water-soluble compound salt to ion-exchanged water and stirring and mixing for 12 hours.

TABLE 4

|  | B-1 | B-2 | B-3 | B-4 | B-5 |
|---|---|---|---|---|---|
| Yttrium acetate (g) | 10 | 1 | 50 | | |
| Yttrium chloride (g) | | | | 10 | |
| Calcium acetate (g) | | | | | 10 |
| Magnesium acetate (g) | | | | | |
| Lanthanum chloride (g) | | | | | |
| Ion exchanged water (g) | 90 | 99 | 50 | 90 | 90 |
| Concentration of stabilizing material containing liquid (wt %) | 10 | 1 | 50 | 10 | 10 |

TABLE 5

|  | B-6 | B-7 | B-8 | B-9 | B-10 |
|---|---|---|---|---|---|
| Yttrium acetate (g) | | | 5 | 0.5 | 55 |
| Yttrium chloride (g) | | | | | |
| Calcium acetate (g) | | | | | |
| Magnesium acetate (g) | 10 | | | | |
| Lanthanum chloride (g) | | 10 | 5 | | |
| Ion exchanged water (g) | 90 | 90 | 90 | 99.5 | 45 |
| Concentration of stabilizing material containing liquid (wt %) | 10 | 10 | 5 | 0.5 | 55 |

The preliminary bodies of zirconia mill blank for dental cutting and machining (A-1) to (A-14) were impregnated with a solution of the water-soluble compound salt by the following impregnation method to obtain zirconia mill blanks for dental cutting and machining. The preliminary bodies of zirconia mill blank for dental cutting and machining (A-15) to (A-21) were directly used as zirconia mill blanks for dental cutting and machining.

[Impregnation Method]

Impregnation Method (C-1)

The preliminary bodies of zirconia mill blank for dental cutting and machining was immersed in each solution of the water-soluble compound salt for 1 hour under a normal pressure atmosphere. Thereafter, the preliminary bodies of zirconia mill blank for dental cutting and machining was taken out from the solution of the water-soluble compound salt solution and dried (110° C., 12 hours) under a normal pressure environment.

Impregnation Method (C-2)

The preliminary bodies of zirconia mill blank for dental cutting and machining was immersed in each solution of the water-soluble compound salt for 120 hours under a normal pressure atmosphere. Thereafter, the preliminary bodies of zirconia mill blank for dental cutting and machining was taken out from the solution of the water-soluble compound salt solution and dried (110° C., 12 hours) under a normal pressure environment.

Impregnation Method (C-3)

The preliminary bodies of zirconia mill blank for dental cutting and machining was immersed in each solution of the water-soluble compound salt for 8 hours under a normal pressure atmosphere. Thereafter, the preliminary bodies of zirconia mill blank for dental cutting and machining was taken out from the solution of the water-soluble compound salt solution and dried (110° C., 12 hours) under a normal pressure environment.

Impregnation Method (C-4)

The preliminary bodies of zirconia mill blank for dental cutting and machining was immersed in each solution of the water-soluble compound salt for 8 hours under a reduced pressure atmosphere (−720 mmHg). Thereafter, the preliminary bodies of zirconia mill blank for dental cutting and machining was taken out from the solution of the water-soluble compound salt solution and dried (110° C., 12 hours) under a normal pressure environment.

Impregnation Method (C-5)

The preliminary bodies of zirconia mill blank for dental cutting and machining was immersed in each solution of the water-soluble compound salt for 8 hours under a pressurized atmosphere (0.5 MPa). Thereafter, the preliminary bodies of zirconia mill blank for dental cutting and machining was taken out from the solution of the water-soluble compound salt solution and dried (110° C., 12 hours) under a normal pressure environment.

Impregnation Method (C-6)

The preliminary bodies of zirconia mill blank for dental cutting and machining was immersed in each solution of the water-soluble compound salt for 8 hours under a normal pressure atmosphere. Thereafter, the preliminary bodies of zirconia mill blank for dental cutting and machining was taken out from the solution of the water-soluble compound salt solution and dried (500° C., 12 hours) under a high-temperature environment.

Impregnation Method (C-7)

The preliminary bodies of zirconia mill blank for dental cutting and machining was immersed in each solution of the water-soluble compound salt for 8 hours under a normal pressure atmosphere. Thereafter, the preliminary bodies of zirconia mill blank for dental cutting and machining was taken out from the solution of the water-soluble compound salt solution and dried (600° C., 12 hours) under a high-temperature environment.

Table 6 shows a preparing method in which the preliminary body of zirconia mill blank for dental cutting and machining was immersed in each stabilizing material-containing liquid and dried.

TABLE 6

|  | C-1 | C-2 | C-3 | C-4 | C-5 | C-6 | C-7 |
|---|---|---|---|---|---|---|---|
| Impregnation method | Normal pressure | Normal pressure | Normal pressure | Reduced pressure | Pressurized | Normal pressure | Normal pressure |
| Impregnation Time (h) | 1 | 120 | 8 | 8 | 8 | 8 | 8 |
| Dry time(h) | 12 | 12 | 12 | 12 | 12 | 12 | 12 |
| Dry temperature (° C.) | 110 | 110 | 110 | 110 | 110 | 500 | 600 |

[Evaluation of Content of Water-Soluble Compound Salt]

The test specimen for evaluating the content of the water-soluble compound salt was prepared by cutting and machining the zirconia mill blank for dental cutting and machining prepared by each impregnation method into a round plate shape (φ4 mm×1.6 mm). Each test specimen was quantitatively analyzed by using a fluorescent X-ray apparatus (manufactured by Rigaku Corporation). The content of the water-soluble compound salt was calculated in terms of oxide. The supported amount of the water-soluble compound salt was calculated from the following formula. The test specimen for evaluating a molar fraction o of the ceramic particle semi-fired body was prepared by cutting and machining into a round plate shape (φ14 mm×1.6 mm). Each test specimen was quantitatively analyzed using a fluorescent X-ray apparatus (manufactured by Rigaku Corporation). The content of stabilizing material was calculated in terms of oxide, and the molar fraction of the zirconium oxide and the stabilizing material were calculated. Furthermore, the zirconia mill blank for dental cutting and machining prepared by each preparing method was cut and machined into a round plate shape (φ14 mm×1.6 mm) to prepare test specimens. Each test specimen was quantitatively analyzed using a fluorescent X-ray apparatus (manufactured by Rigaku Corporation). At this time, the ratio of the zirconium oxide and the stabilizing material in the ceramic particle semi-fired body was obtained from the molar fraction of the zirconium oxide in the zirconia mill blank for dental cutting and machining, and the molar amount of the stabilizing material was calculated. Thereafter, based on this amount, the molar amount of only the water-soluble compound was identified by subtracting the molar amount of the stabilizing material from the total amount of the stabilizing material and the water-soluble compound obtained by fluorescent X-ray later.

An example of specific calculation is shown below. Ceramic particles semi-fired body (molar fraction: zirconium oxide: 96.00 mol %, yttrium oxide: 3.00 mol %, others: 1.00 mol %) is impregnated with yttrium acetate to obtain the zirconia mill blank for dental cutting and machining. As a result of analysis of the zirconia mill blank for dental cutting and machining, zirconium oxide: 94.00 mol %, yttrium oxide: 5.00 mol %, others: 1.00 mol %. In this case, the supported amount of water-soluble yttrium is calculated as follows.

Supported amount of water-soluble yttrium=5.00−3.00×(94.00÷96.00)=2.06 mol %

Note that the amount of yttrium oxide in the analysis result of the zirconia mill blank for dental cutting and machining in the above calculation example includes yttrium acetate converted to yttrium oxide.

[Evaluation of Translucency (Evaluation of Contrast Ratio)]

The test specimen for evaluating the translucency was prepared by cutting and machining the zirconia mill blank for dental cutting and machining into a round plate shape (φ14 mm×1.6 mm). Each specimen was perfect fired (1600° C., 2 hours) in a firing furnace. Then, the thickness (1.0 mm) of each test body was adjusted with a surface grinder. The translucency was evaluated by measuring the contrast ratio. The contrast ratio was measured by using a spectrocolorimeter (manufactured by Konica Minolta). In the following formula, $Y_w$ is the value Y measured by placing the white plate under the test specimen, and $Y_b$ is the value Y measured by placing the black plate under the test specimen. The contrast ratio was calculated from the following formula.

The contrast ratio=$Y_b/Y_w$

When the contrast ratio value is close to zero, the materials are transparency. When the contrast ratio value is close to 1, the materials are opaqueness.

[Evaluation of Bending Strength]

The bending test specimen was prepared by cutting and machining the zirconia mill blank for dental cutting and machining into a plate shape (width: 4.8 mm×length: 20 mm×thickness: 1.6 mm). Each test specimen was perfect sintered (1600° C., 2 hours) in a firing furnace. Thereafter, the size of each test specimen (width: 4.0 mm×length: 16 mm×thickness: 1.2 mm) was adjusted with a surface grinder. The bending test was performed in accordance with ISO6872 (span distance: 12 mm, crosshead speed: 1.0 mm/min).

[Evaluation of Uniformity of Water-Soluble Compound Salt]

The test specimen for evaluating the uniformity of water-soluble compound salt was prepared by cutting machining the zirconia mill blank for dental cutting and machining into a plate shape (φ14 mm×1.6 mm). From each test specimen, a portion having a diameter of 1 mm from the center of the round plate-like surface was cut into a columnar shape (height 1.6 mm), and 0.12 mm±0.01 mm portion and 0.40 mm±0.01 mm portion from the round plate-like surface of the cut column were cut out, and the amount of the water-soluble compound salt contained in the cut-out portion was quantitatively analyzed using a fluorescent X-ray apparatus (manufactured by Rigaku Corporation). Uniformity of water-soluble compound salt was evaluated from the following formula.

Uniformity (%)=(0.40 mm±0.01 mm portion content)/(0.12 mm±0.01 mm portion content)

Tables 7 to 12 show the characteristic test results of the prepared zirconia mill blank for dental cutting and machining.

TABLE 7

| | Example 1 | Example 2 | Example 3 | Example 4 | Example 5 | Example 6 |
|---|---|---|---|---|---|---|
| Zirconia mill blanks for dental cutting and machining | A-1 | A-2 | A-3 | A-4 | A-5 | A-6 |
| Amount of stabilizing material in preliminary body of zirconia mill blank for dental cutting and machining (mol %) | 3 | 3 | 3 | 5.5 | 6.5 | 5.5 |
| Solution of water-soluble compound salt | BI | B-1 | B-1 | B-1 | B-1 | B-1 |
| Impregnation Method | C-1 | C-1 | C-1 | C-1 | C-1 | C-1 |
| Amount of water-soluble compound salt (mol %) | 0.79 | 0.81 | 0.16 | 0.84 | 0.83 | 0.84 |
| Total amount of stabilizing material and water-soluble compound in Zirconia mill blanks for dental cutting and machining (mol %) | 3.8 | 3.8 | 3.2 | 6.3 | 7.3 | 6.3 |
| Contrast ratio | 0.76 | 0.76 | 0.76 | 0.73 | 0.71 | 0.72 |
| Bending strength (MPa) | 1458 | 1442 | 1461 | 1062 | 886 | 1059 |
| Uniformity (%) | 100 | 100 | 100 | 100 | 100 | 100 |

TABLE 8

| | Example 7 | Example 8 | Example 9 | Example 10 | Example 11 | Example 12 |
|---|---|---|---|---|---|---|
| Zirconia mill blanks for dental cutting and machining | A-1 | A-1 | A-1 | A-1 | A-1 | A-1 |
| Amount of stabilizing material in preliminary body of zirconia mill blank for dental cutting and machining (mol %) | 3 | 3 | 3 | 3 | 3 | 3 |
| Solution of water-soluble compound salt | B-2 | B-3 | B-4 | B-5 | B-6 | B-7 |
| Impregnation Method | C-1 | C-1 | C-1 | C-1 | C-1 | C-1 |
| Amount of water-soluble compound salt (mol %) | 0.27 | 2.63 | 1.16 | 0.7 | 0.82 | 1.05 |
| Total amount of stabilizing material and water-soluble compound in Zirconia mill blanks for dental cutting and machining (mol %) | 3.3 | 5.6 | 4.2 | 3.7 | 3.8 | 4 |
| Contrast ratio | 0.76 | 0.73 | 0.75 | 0.75 | 0.75 | 0.74 |
| Bending strength (MPa) | 1486 | 1013 | 1333 | 1428 | 1293 | 1431 |
| Uniformity (%) | 100 | 100 | 100 | 100 | 100 | 100 |

TABLE 9

| | Example 13 | Example 14 | Example 15 |
|---|---|---|---|
| Zirconia mill blanks for dental cutting and machining | A-1 | A-1 | A-1 |
| Amount of stabilizing material in preliminary body of zirconia mill blank for dental cutting and machining (mol %) | 3 | 3 | 3 |
| Solution of water-soluble compound salt | B-8 | B-9 | B-10 |
| Impregnation Method | C-1 | C-1 | C-1 |
| Amount of water-soluble compound salt (mol %) | 0.34 | 0.11 | 2.89 |
| Total amount of stabilizing material and water-soluble compound in Zirconia mill blanks for dental cutting and machining (mol %) | 3.3 | 3.1 | 5.9 |

TABLE 9-continued

|  | Example 13 | Example 14 | Example 15 |
|---|---|---|---|
| Contrast ratio | 0.76 | 0.76 | 0.73 |
| Bending strength (MPa) | 1481 | 1466 | 980 |
| Uniformity (%) | 100 | 100 | 100 |

TABLE 10

|  | Example 16 | Example 17 | Example 18 | Example 19 | Example 20 | Example 21 |
|---|---|---|---|---|---|---|
| Zirconia mill blanks for dental cutting and machining | A-1 | A-1 | A-1 | A-1 | A-1 | A-1 |
| Amount of stabilizing material in preliminary body of zirconia mill blank for dental cutting and machining (mol %) | 3 | 3 | 3 | 3 | 3 | 3 |
| Solution of water-soluble compound salt | B-1 | B-1 | B-1 | B-1 | B-1 | B-1 |
| Impregnation Method | C-2 | C-3 | C-4 | C-5 | C-6 | C-7 |
| Amount of water-soluble compound salt (mol %) | 0.79 | 0.78 | 0.79 | 0.8 | 0.79 | 0.79 |
| Total amount of stabilizing material and water-soluble compound in Zirconia mill blanks for dental cutting and machining (mol %) | 3.8 | 3.8 | 3.8 | 3.8 | 3.8 | 3.8 |
| Contrast ratio | 0.76 | 0.76 | 0.76 | 0.76 | 0.76 | 0.76 |
| Bending strength (MPa) | 1458 | 1441 | 1467 | 1445 | 1421 | 1430 |
| Uniformity (%) | 100 | 100 | 100 | 100 | 100 | 100 |

TABLE 11

|  | Example 22 | Example 23 | Example 24 | Example 25 |
|---|---|---|---|---|
| Zirconia mill blanks for dental cutting and machining | A-7 | A-8 | A-9 | A-10 |
| Amount of stabilizing material in preliminary body of zirconia mill blank for dental cutting and machining (mol %) | 2 | 7 | 3 | 3 |
| Solution of water-soluble compound salt | B-4 | B-1 | B-1 | B-1 |
| Impregnation Method | C-1 | C-1 | C-1 | C-1 |
| Amount of water-soluble compound salt (mol %) | 1.04 | 0.78 | 0.82 | 0.11 |
| Total amount of stabilizing material and water-soluble compound in Zirconia mill blanks for dental cutting and machining (mol %) | 3 | 7.8 | 3.8 | 3.1 |

TABLE 11-continued

|  | Example 22 | Example 23 | Example 24 | Example 25 |
|---|---|---|---|---|
| Contrast ratio | 0.76 | 0.69 | 0.76 | 0.76 |
| Bending strength (MPa) | 1434 | 595 | 1340 | 1456 |
| Uniformity (%) | 100 | 100 | 100 | 100 |

TABLE 12

|  | Example 26 | Example 27 | Example 28 | Example 29 | Example 30 |
|---|---|---|---|---|---|
| Zirconia mill blanks for dental cutting and machining | A-15 | A-16 | A-17 | A-18 | A-19 |
| Amount of stabilizing material in preliminary body of zirconia mill blank for dental cutting and machining (mol %) | 6.3 | 6.3 | 6.3 | 6.3 | 6.3 |
| Solution of water-soluble compound salt | — | — | — | — | — |
| Impregnation Method | — | — | — | — | — |
| Amount of water-soluble compound salt (mol %) | 0.1 | 0.5 | 3 | 3 | 3.5 |
| Total amount of stabilizing material and water-soluble | 6.4 | 6.8 | 9.3 | 9.3 | 9.8 |

TABLE 12-continued

|  | Example 26 | Example 27 | Example 28 | Example 29 | Example 30 |
|---|---|---|---|---|---|
| compound in Zirconia mill blanks for dental cutting and machining (mol %) |  |  |  |  |  |
| Contrast ratio | 0.69 | 0.69 | 0.66 | 0.66 | 0.65 |
| Bending strength (MPa) | 591 | 592 | 565 | 551 | 545 |
| Uniformity (%) | 100 | 100 | 100 | 100 | 100 |

TABLE 13

|  | Example 31 | Example 32 | Example 33 |
|---|---|---|---|
| Zirconia mill blanks for dental cutting and machining | A-21 | A-11 | A-12 |
| Amount of stabilizing material in preliminary body of zirconia mill blank for dental cutting and machining (mol %) | 3 | 3 | 3 |
| Solution of water-soluble compound salt | — | — | — |
| Impregnation Method | — | — | — |
| Amount of water-soluble compound salt (mol %) | 2.6 | 3.3 | 1 |
| Total amount of stabilizing material and water-soluble compound in Zirconia mill blanks for dental cutting and machining (mol %) | 5.6 | 6.3 | 4 |
| Contrast ratio | 0.74 | 0.74 | 0.76 |
| Bending strength (MPa) | 920 | 839 | 1140 |
| Uniformity (%) | 100 | 100 | 100 |

TABLE 14

|  | Comparative Example 1 | Comparative Example 2 | Comparative Example 3 | Comparative Example 4 |
|---|---|---|---|---|
| Zirconia mill blanks for dental cutting and machining | A-14 | A-13 | A-20 | A-7 |
| Amount of stabilizing material in preliminary body of zirconia mill blank for dental cutting and machining (mol %) | 1 | 8 | 6.3 | 2 |
| Solution of water-soluble compound salt | B-1 | — | — | — |
| Impregnation Method | C-1 | — | — | — |
| Amount of water-soluble compound salt (mol %) | 0.79 | — | 4 | — |
| Total amount of stabilizing material and water-soluble compound in Zirconia mill blanks for dental cutting and machining (mol %) | 1.8 | 8 | 10.6 | 2 |
| Contrast ratio | 0.81 | 0.71 | 0.66 | 0.81 |
| Bending strength (MPa) | 1456 | 442 | 464 | 1431 |
| Uniformity (%) | 100 | 100 | 100 | 100 |

In the Examples 1 to 33 in which the content of the stabilizing material in the preliminary body of zirconia mill blank for dental cutting and machining (ceramic particles semi-fired body) was within a range of 2 to 7 mol %, and the content of the water-soluble compound salt in the zirconia mill blank for dental cutting and machining was within a range of 0.1 to 3.5 mol %, the contrast ratio was 0.76 or less, the bending strength was 500 or more, and therefore it was recognized that both bending strength and translucency can be achieved at a high level.

On the other hand, in the Comparative Examples 1 to 4 in which the content of the stabilizing material in the preliminary body of zirconia mill blank for dental cutting and machining (ceramic particles semi-fired body) was not within a range of 2 to 7 mol %, or the content of the water-soluble compound salt in the zirconia mill blank for dental cutting and machining was not within a range of 0.1 to 3.5 mol %, the contrast ratio was 0.78 or more or the bending strength was less than 500, and therefore it was recognized that both bending strength and translucency cannot be achieved at a high level.

Next, examples of the transparency improving liquid of the present invention will be described.

[Preparation of Transparency Improvement Liquid]

Tables 15 to 20 show composition tables of transparency improvement liquids according to Examples, Comparative examples, and Reference examples. The transparency improving liquids according to Examples, Comparative examples, and Reference examples are prepared by adding (a) water-soluble compound salts that salt that is not an oxide (excluding the cerium compound), (b) water and/or vegetable oil, (c) water-soluble cerium compound and (d)

water-soluble organic solvent and mixed for 12 hours. The compositions in the tables are given in wt. % unless otherwise specified.

[Zirconia Mill Blank for Dental Cutting and Machining for Test Specimen]

A zirconia disk containing 3 mol % of stabilizing material and a zirconia disk containing 5 mol % of stabilizing material were prepared as the zirconia mill blank for dental cutting and machining. The zirconia disk was processed into the size required for the following test and used for the test. Table 18 shows the test results of the zirconia disk not using the transparency improving liquid of the present invention as Reference examples 1 and 2.

[Preparation of Transmittance Test Body]

In measuring the transmittance, the pre-fired product (stabilizing material (yttrium) amount: 3 mol % and 5 mol %) was prepared by molding Tosoh zirconia powder and pre-fired at 1100° C. as a zirconia mill blank for dental cutting and machining, and a specimen having a diameter of 14 mm and a thickness of 1.6 mm was prepared by cutting and machining the the zirconia mill blank for dental cutting and machining. This test specimen was applied with 1 g of the transparency improving liquid described in each Example for 10 minutes and sufficiently dried at 80° C. for 1 hour. Then, according to the method described in the instruction manual, the resultant was sintered by keeping for 2 hours at a final keeping temperature of 1450° C. Thereafter, the test specimen was adjusted to a thickness of 1.0 mm, and the visible light transmittance was measured.

[Preparation of Bending Test Specimen]

In measurement of the bending test specimen, a test specimen having a width of 4.8 mm, a thickness of 1.6 mm, and a length of 20 mm was prepared by cutting and machining the zirconia mill blank for dental cutting and machining prepared in the Transmittance test. This test specimen was applied with 1 g of the transparency improving liquid described in each Example for 10 minutes and sufficiently dried at 80° C. for 1 hour. Then, according to the method described in the instruction manual, the resultant was sintered by keeping for 2 hours at a final keeping temperature of 1450° C. Thereafter, the test specimen was adjusted to a thickness of 1.2 mm, and a three-point bending test was performed. The test method conformed to ISO6872.

[Color Measurement of Color Tone]

In measuring the color tone, a test specimen having a width of 10 mm, a thickness of 1.6 mm, and a length of 10 mm was prepared by cutting and machining the zirconia mill blank for dental cutting and machining prepared in the Transmittance test. This test specimen was applied with 1 g of the transparency improving liquid described in each Example for 10 minutes and sufficiently dried at 80° C. for 1 hour. Then, according to the method described in the instruction manual, the resultant was sintered by keeping for 2 hours at a final keeping temperature of 1450° C. Thereafter, the test specimen was adjusted to a thickness of 1.0 mm, and the $L^*$ value, $a^*$ value, and $b^*$ value were measured with a white back using a Konica Minolta colorimeter.

TABLE 15

|  |  | Example 34 | Example 35 | Example 36 | Example 37 | Example 38 | Example 39 |
|---|---|---|---|---|---|---|---|
| Component(a): Yttrium chloride | | 20 | 40 | 60 | 30 | 30 | 30 |
| Component(b): Water | | 67 | 47 | 27 | 55 | 40 | 50 |
| Component(c): Cerium chloride | | 3 | 3 | 3 | 5 | 10 | 10 |
| Component(d): Polyethylene glycol (Molecular weight: 200) | | 10 | 10 | 10 | 10 | 20 | 10 |
| Red cabbage pigment | | 1 ppm | 1 ppm | 1 ppm | 1 ppm | 1 ppm | 1 ppm |
| Amount of stabilizing material (yttrium) of used zirconia for dental cutting and machning (mol %) | | 3 | 3 | 3 | 3 | 3 | 3 |
| Visible light transmittance (%) | | 35 | 37 | 39 | 39 | 35 | 41 |
| Value of color | $L^*$ | 88.8 | 89.8 | 90.1 | 89.8 | 89.8 | 89.8 |
| (White back color) | $a^*$ | −0.23 | −0.84 | 0.18 | −0.45 | 1.21 | −1.15 |
| | $b^*$ | 17.65 | 16.94 | 17.13 | 17.85 | 20.6 | 20.56 |
| Bending strength (Mpa) | | 1170 | 1100 | 1050 | 1185 | 1190 | 1172 |

TABLE 16

|  |  | Example 40 | Example 41 | Example 42 | Example 43 | Example 44 |
|---|---|---|---|---|---|---|
| Component(a): Yttrium chloride | | | | 20 | 40 | 60 |
| Component(a): Yttrium nitrate | | 20 | 20 | | | |
| Component(b): Water | | 69.9 | 60 | 67 | 47 | 27 |
| Component(c): Cerium chloride | | 0.1 | 3 | 3 | 3 | 3 |
| Component(d): Ethanol | | | 7 | | | |
| Component(d): Polyethylene glycol (Molecular weight: 200) | | 10 | 10 | 10 | 10 | 10 |
| Red cabbage pigment | | 1 ppm | 1 ppm | 1 ppm | 1 ppm | 1 ppm |
| Amount of stabilizing material (yttrium) of used zirconia for dental cutting and machning (mol %) | | 3 | 3 | 5 | 5 | 5 |
| Visible light transmittance (%) | | 34 | 34 | 41 | 45 | 47 |
| Value of color | $L^*$ | 89.1 | 89.2 | 75 | 72 | 72.4 |
| (White back color) | $a^*$ | 0.03 | 0.05 | 0.86 | 0.75 | 0.65 |
| | $b^*$ | 17.23 | 17.32 | 12.5 | 11.5 | 10.5 |
| Bending strength (Mpa) | | 1170 | 1050 | 905 | 920 | 930 |

TABLE 17

|  | Example 45 | Example 46 | Example 47 | Example 48 | Example 49 | Example 50 |
|---|---|---|---|---|---|---|
| Component(a): Yttrium chloride | 20 |  | 10 | 70 | 20 | 10 |
| Component(a): Yttrium 2-ethylhexanoate |  | 20 |  |  |  |  |
| Component(b): Water | 30 |  | 19 | 19 | 76.5 | 80 |
| Component(b): Limonene | 30 | 60 |  |  |  |  |
| Component(c): Cerium chloride | 3 |  | 70 | 10 | 3 | 2 |
| Component(c): Cerium 2-ethylhexoate |  | 3 |  |  |  |  |
| Component(d): Polyethylene glycol (Molecular weight: 200) | 17 | 17 | 1 | 1 | 0.5 | 8 |
| Red cabbage pigment | 1 ppm | 1 ppm | 1 ppm | 1 ppm | 1 ppm | 1 ppm |
| Amount of stabilizing material (yttrium) of used zirconia for dental cutting and machning (mol %) | 3 | 3 | 3 | 3 | 3 | 3 |
| Visible light transmittance (%) | 35 | 34 | 36 | 36 | 31 | 30 |
| Value of color L* | 89.1 | 88 | 88 | 88 | 87.9 | 87.8 |
| (White back color) a* | 0.03 | 0.04 | 1.2 | 0.05 | 0.04 | 0.86 |
| b* | 17.5 | 18.5 | 20.1 | 17 | 18.4 | 17.5 |
| Bending strength (Mpa) | 1150 | 1105 | 1151 | 1175 | 1100 | 1105 |

TABLE 18

|  | Example 51 | Example 52 | Example 53 | Example 54 | Example 55 | Example 56 |
|---|---|---|---|---|---|---|
| Component(a): Yttrium chloride | 80 | 70 | 12 | 10 | 10 | 20 |
| Component(a): Yttrium 2-ethylhexanoate |  |  |  |  |  |  |
| Component(b): Water | 16 | 8 | 86 | 86 | 10 | 76.9 |
| Component(b): Limonene |  |  |  |  |  |  |
| Component(c): Cerium chloride | 3 | 21 | 2 | 2 | 80 | 3 |
| Component(c): Cerium 2-ethylhexoate |  |  |  |  |  |  |
| Component(d): Polyethylene glycol (Molecular weight: 200) | 1 | 1 |  | 2 |  | 0.1 |
| Red cabbage pigment | 1 ppm | 1 ppm | 1 ppm | 1 ppm |  |  |
| Amount of stabilizing material (yttrium) of used zirconia for dental cutting and machning (mol %) | 3 | 3 | 3 | 3 | 3 | 3 |
| Visible light transmittance (%) | 42 | 41 | 33 | 33 | 33 | 34 |
| Value of color L* | 89.8 | 88.1 | 88.7 | 88.6 | 88.7 | 88.9 |
| (White back color) a* | 0.03 | 0.04 | 0.04 | 0.03 | 0.03 | 0.03 |
| b* | 12.3 | 18.5 | 13.4 | 12.9 | 19.4 | 12.9 |
| Bending strength (Mpa) | 1040 | 1039 | 1121 | 1165 | 1121 | 1151 |

TABLE 19

|  | Reference example 1 (not using transparency improving liquid) | Reference example 2 (not using transparency improving liquid) | Comparative Example 5 |
|---|---|---|---|
| Component(a): Yttrium chloride |  |  |  |
| Component(a): Yttrium 2-ethylhexanoate |  |  |  |
| Component(b): Water |  |  | 80 |
| Component(c): Cerium chloride |  |  | 10 |
| Component(d): Polyethylene glycol (Molecular weight: 200) |  |  | 10 |
| Red cabbage pigment |  |  | 1 ppm |
| Amount of stabilizing material (yttrium) of used zirconia for dental cutting and machning (mol %) | 3 | 5 | 3 |
| Visible light transmittance (%) | 28 | 41 | 29 |
| Value of color L* | 88.7 | 74.1 | 88.5 |
| (White back color) a* | 0.96 | 1.23 | −0.69 |
| b* | 17.39 | 15.3 | 25.83 |
| Bending strength (Mpa) | 1210 | 1170 | 1170 |

TABLE 20

|  | Comparative Example 6 | Comparative Example 7 | Comparative Example 8 | Comparative Example 9 | Comparative Example 10 |
|---|---|---|---|---|---|
| Component(a): Yttrium chloride | 60 | 5 | 10 | 85 | 20 |
| Component(b): Water | 29 | 75 | 4 | 10 | 30 |
| Component(c): Cerium chloride | 1 | 10 | 85 | 3 | 20 |

TABLE 20-continued

|  | Comparative Example 6 | Comparative Example 7 | Comparative Example 8 | Comparative Example 9 | Comparative Example 10 |
|---|---|---|---|---|---|
| Component(d): Polyethylene glycol (Molecular weight: 200) | 10 | 10 | 1 | 2 | 30 |
| Red cabbage pigment | 1 ppm | 1 ppm | 1 ppm | 1 ppm | 1 ppm |
| Amount of stabilizing material (yttrium) of used zirconia for dental cutting and machning (mol %) | 3 | 3 | 3 | 3 | 3 |
| Visible light transmittance (%) | 35 | 28 | 37 | 39 | 28 |
| Value of color         L* | 82.8 | 88.5 | 81.7 | 82.8 | 88.9 |
| (White back color)    a* | 0.14 | 0.77 | 0.16 | 0.17 | 0.79 |
|                       b* | 17.39 | 14.6 | 17.12 | 18.39 | 14.65 |
| Bending strength (Mpa) | 705 | 1100 | 590 | 570 | 1100 |

In Examples 34 to 41 and 45 to 56, the visible light transmittance was 30% or more and the bending strength was 900 MPa or more. Therefore, the visible light transmittance can be improved without significantly reducing the strength as compared with Reference example (not using transparency improving liquid). Similarly, in Examples 42 to 44, a visible light transmittance of 30% or more and a bending strength of 900 MPa or more were exhibited. Therefore, the visible light transmittance can be improved without significantly reducing the strength as compared with Reference example (not using transparency improving liquid). Since Comparative Example 5 has no component (a), the visible light transmittance is hardly improved as compared with the Reference Example 1. In Comparative Examples 6, 8, and 9, the transparency is clinically sufficient, but the decrease in bending strength is significant. In Comparative Examples 7 and 10, there is no reduction in strength, but the transparency is not sufficient.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

INDUSTRIAL APPLICABILITY

According to the present invention, a zirconia perfect sintered body which has a chroma of an excellent color tone and excellent translucency as compared with a zirconia mill blank for dental cutting and machining prepared from a zirconia raw material powder containing various stabilizing materials while maintaining high strength, and does not cause deformation can be provided.

The invention claimed is:
1. A zirconia mill blank for dental cutting and machining for preparing a prosthesis device by cutting and machining, wherein,
the zirconia mill blank for dental cutting and machining is a semi-fired zirconia mill blank for dental cutting and machining containing a semi-fired body of a ceramic particle,
the ceramic particle contains zirconium oxide, and 2 to 7 mol % of a stabilizing material consisting of an oxide in terms of the oxide,
the zirconia mill blank for dental cutting and machining contains a water-soluble compound salt which contains at least one element selected from the group consisting of calcium, magnesium and a rare earth element and is not an oxide,
the water-soluble compound salt is supported on a surface of the semi-fired body of the ceramic particle,
a content of the water-soluble compound salt in the zirconia mill blank for dental cutting and machining is within a range of 0.1 to 3.5 mol %, and
the water-soluble compound salt contains an organic acid salt of yttrium.
2. The zirconia mill blank for dental cutting and machining according to claim 1, wherein,
a content of the water-soluble compound salt in a position spaced from a surface of the zirconia mill blank for dental cutting and machining by 45 to 55% of a dimension between the surface of the zirconia mill blank for dental cutting and machining and the center of gravity of the zirconia mill blank for dental cutting and machining in a direction from the surface toward the center of gravity of the zirconia mill blank for dental cutting and machining is within a range of 50 to 150% of a content of the water-soluble compound salt in a position spaced from the surface of the zirconia mill blank for dental cutting and machining by 10 to 20% of the dimension between the surface of the zirconia mill blank for dental cutting and machining and the center of gravity of the zirconia mill blank for dental cutting and machining.
3. The zirconia mill blank for dental cutting and machining according to claim 1, wherein,
the zirconia mill blank for dental cutting and machining contains Pr, Er, Fe, Co, Ni, Mn or Cu as a coloring material.
4. The zirconia mill blank for dental cutting and machining according to claim 1, wherein,
the zirconia mill blank for dental cutting and machining consists of a plurality of layers having different contents of the stabilizing material consisting of the oxide and/or the coloring material.
5. The zirconia mill blank for dental cutting and machining according to claim 1, wherein,
The zirconia mill blank for dental cutting and machining has a disk shape or a block shape.
6. A dental prosthetic device prepared from the zirconia mill blank for dental cutting and machining according to claim 1.
7. The zirconia mill blank for dental cutting and machining according to claim 1,
wherein the water-soluble compound salt is contained in a transparency improving liquid comprising:

a (a) solution of the water-soluble compound salt that is not an oxide, excluding a water-soluble cerium compound: 10 to 80 wt. %, and a (b) water: 20 to 90.

8. The zirconia mill blank for dental cutting and machining according to claim 7, wherein the water-soluble compound salt is supported on the surface of the semi-fired body of the ceramic particle by a method comprising;

applying the transparency improving liquid to the zirconia mill blank for dental cutting and machining or immersing the zirconia mill blank for dental cutting and machining in the transparency improving liquid, to support the water-soluble compound salt that is not an oxide on the surface of the semi-fired body of the ceramic particle.

9. The zirconia mill blank for dental cutting and machining according to claim 8, wherein, the zirconia mill blank for dental cutting and machining contains iron.

10. The zirconia mill blank for dental cutting and machining according to claim 8, wherein, the zirconia mill blank for dental cutting and machining contains yttrium and/or erbium.

11. The zirconia mill blank for dental cutting and machining according to claim 10, wherein, a molar concentration of yttrium and/or erbium in the zirconia mill blank for dental cutting and machining is 4 mol % or less.

12. The zirconia mill blank for dental cutting and machining according to claim 8, wherein, the transparency improving liquid is applied only on a surface layer of the dental prosthetic device cut from the zirconia mill blank for dental cutting and machining.

13. The zirconia mill blank for dental cutting and machining according to claim 12, wherein, the dental prosthetic device is an inlay, a laminate, a crown, or a bridge.

14. The zirconia mill blank for dental cutting and machining according to claim 1, wherein the water-soluble compound salt is contained in a transparency improving liquid comprising:

a (a) solution of the water-soluble compound salt that is not an oxide, excluding a water-soluble cerium compound: 10 to 80 wt. %, a (b) water: 8 to 86, and a (c) water-soluble cerium compound: 2 to 80 wt. %.

15. The zirconia mill blank for dental cutting and machining according to claim 1, wherein the water-soluble compound salt is contained in a transparency improving liquid comprising:

a (a) solution of the water-soluble compound salt that is not an oxide, excluding a water-soluble cerium compound: 10 to 80 wt. %, a (b) water and/or vegetable oil: 8 to 86, a (c) water-soluble cerium compound: 2 to 80 wt. %, and a (d) water-soluble organic solvent: 0.1 to 20 wt. %.

16. The zirconia mill blank for dental cutting and machining according to claim 15, wherein, the water-soluble organic solvent (d) is any one selected from the group consisting of alcohols, polyols and glycol ethers.

17. The zirconia mill blank for dental cutting and machining according to claim 15, wherein, the total content of the water-soluble compound salt that is not an oxide, excluding the water-soluble cerium compound (a) and the water-soluble cerium compound (c) is within a range of 30 to 70 wt. %.

18. A preparing method of a zirconia mill blank for dental cutting and machining according to claim 1, comprising the following steps (1) and/or (2);

(1) semi-firing the ceramic particle containing zirconium oxide, 2 to 7 mol % of the stabilizing material consisting of an oxide, and 0.1 to 3.5 mol % of the water-soluble compound salt which contains at least one element selected from the group consisting of calcium, magnesium and a rare earth element and is not an oxide, (2) semi-firing the a-ceramic particle containing zirconium oxide and 2 to 7 mol % of the stabilizing material consisting of an oxide, and impregnating the zirconia mill blank for dental cutting and machining containing the semi-fired ceramic particle with a solution of the water-soluble compound salt which contains at least one element selected from the group consisting of calcium, magnesium and a rare earth element and is not an oxide.

19. The preparing method of a zirconia mill blank for dental cutting and machining according to claim 18 including at least the step (2), wherein, the zirconia mill blank for dental cutting and machining containing the semi-fired ceramic particle is dried after impregnating with the solution of the water-soluble compound salt.

20. The preparing method of a zirconia mill blank for dental cutting and machining according to claim 18 including at least the step (2), wherein, the solution of the water-soluble compound salt contains a water-soluble cerium compound.

21. The preparing method of a zirconia mill blank for dental cutting and machining according to claim 18 including at least the step (2), wherein, the solution of the water-soluble compound salt contains a water-soluble cerium compound, a vegetable oil, and an organic solvent.

22. A preparing method of a dental prosthetic device for preparing a dental prosthetic device from a zirconia mill blank for dental cutting and machining prepared by the preparing method of the zirconia mill blank for dental cutting and machining according to claim 10 including at least the step (2), comprising;

dry cutting the zirconia mill blank for dental cutting and machining into the shape of a dental prosthetic device, and main firing the zirconia mill blank for dental cutting and machining having the shape of a dental prosthetic device.

23. A preparing method of a dental prosthetic device for preparing a dental prosthetic device from a zirconia mill blank for dental cutting and machining prepared by the preparing method of the zirconia mill blank for dental cutting and machining according to claim 18 including at least the step (1), comprising;

cutting the zirconia mill blank for dental cutting and machining into the shape of a dental prosthetic device, and main firing the zirconia mill blank for dental cutting and machining having the shape of a dental prosthetic device.

* * * * *